United States Patent
el Kaliouby et al.

(10) Patent No.: US 11,292,477 B2
(45) Date of Patent: *Apr. 5, 2022

(54) VEHICLE MANIPULATION USING COGNITIVE STATE ENGINEERING

(71) Applicant: Affectiva, Inc., Boston, MA (US)

(72) Inventors: Rana el Kaliouby, Milton, MA (US); Abdelrahman N. Mahmoud, Somerville, MA (US); Panu James Turcot, Pacifica, CA (US); Andrew Todd Zeilman, Beverly, MA (US); Taniya Mishra, New York, NY (US)

(73) Assignee: Affectiva, Inc., Boston, MA (US)

( * ) Notice: Subject to any disclaimer, the term of this patent is extended or adjusted under 35 U.S.C. 154(b) by 345 days.

This patent is subject to a terminal disclaimer.

(21) Appl. No.: 16/429,022

(22) Filed: Jun. 2, 2019

(65) Prior Publication Data
US 2019/0283762 A1 Sep. 19, 2019

Related U.S. Application Data

(63) Continuation-in-part of application No. 15/875,644, filed on Jan. 19, 2018, now Pat. No. 10,627,817, (Continued)

(51) Int. Cl.
*B60W 40/08* (2012.01)
*G06F 3/01* (2006.01)
(Continued)

(52) U.S. Cl.
CPC ............ *B60W 40/08* (2013.01); *G06F 3/013* (2013.01); *G06K 9/00315* (2013.01);
(Continued)

(58) Field of Classification Search
USPC ........................................................ 701/36
See application file for complete search history.

(56) References Cited

U.S. PATENT DOCUMENTS 3,034,500 A 5/1962 Backster, Jr.
3,548,806 A 12/1970 Fisher
(Continued)

FOREIGN PATENT DOCUMENTS

JP 08115367 7/1996
KR 10-2005-0021759 A 3/2005
(Continued)

OTHER PUBLICATIONS

Fasel, B. (Aug. 2002). Robust face analysis using convolutional neural networks. In Object recognition supported by user interaction for service robots (vol. 2, pp. 40-43). IEEE.
(Continued)

*Primary Examiner* — Tyler D Paige
(74) *Attorney, Agent, or Firm* — Adams Intellex, PLC

(57) ABSTRACT

Vehicle manipulation uses cognitive state engineering. Images of a vehicle occupant are obtained using imaging devices within a vehicle. The one or more images include facial data of the vehicle occupant. A computing device is used to analyze the images to determine a cognitive state. Audio information from the occupant is obtained and the analyzing is augmented based on the audio information. The cognitive state is mapped to a loading curve, where the loading curve represents a continuous spectrum of cognitive state loading variation. The vehicle is manipulated, based on the mapping to the loading curve, where the manipulating uses cognitive state alteration engineering. The manipulating includes changing vehicle occupant sensory stimulation. Additional images of additional occupants of the vehicle are obtained and analyzed to determine additional cognitive states. Additional cognitive states are used to adjust the mapping. A cognitive load is estimated based on eye gaze tracking.

26 Claims, 13 Drawing Sheets

Related U.S. Application Data which is a continuation-in-part of application No. 15/273,765, filed on Sep. 23, 2016, now abandoned, which is a continuation-in-part of application No. 14/796,419, filed on Jul. 10, 2015, now abandoned, which is a continuation-in-part of application No. 14/460,915, filed on Aug. 15, 2014, now abandoned, which is a continuation-in-part of application No. 13/153,745, filed on Jun. 6, 2011, now abandoned.

(60) Provisional application No. 62/827,088, filed on Mar. 31, 2019, provisional application No. 62/679,825, filed on Jun. 3, 2018, provisional application No. 62/611,780, filed on Dec. 29, 2017, provisional application No. 62/593,440, filed on Dec. 1, 2017, provisional application No. 62/593,449, filed on Dec. 1, 2017, provisional application No. 62/557,460, filed on Sep. 12, 2017, provisional application No. 62/541,847, filed on Aug. 7, 2017, provisional application No. 62/524,606, filed on Jun. 25, 2017, provisional application No. 62/503,485, filed on May 9, 2017, provisional application No. 62/469,591, filed on Mar. 10, 2017, provisional application No. 62/448,448, filed on Jan. 20, 2017, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.
*G06K 9/00* (2006.01)
*G06N 3/08* (2006.01)
*G06N 5/04* (2006.01)
*G06N 20/00* (2019.01)

(52) U.S. Cl.
CPC ........... *G06K 9/00845* (2013.01); *G06N 3/08* (2013.01); *G06N 5/046* (2013.01); *G06N 20/00* (2019.01); *B60W 2040/0818* (2013.01)

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore., Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ballet |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,724,920 B1 | 4/2004 | Berenz et al. |
| 6,792,458 B1 | 9/2004 | Muret et al. |
| 6,847,376 B2 | 1/2005 | Engeldrum et al. |
| 6,927,694 B1 | 8/2005 | Smith et al. |
| 7,003,135 B2 | 2/2006 | Hsieh et al. |
| 7,013,478 B1 | 3/2006 | Hendricks et al. |
| 7,027,621 B1 | 4/2006 | Prokoski |
| 7,110,570 B1 | 9/2006 | Berenz et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |

(56) References Cited

U.S. PATENT DOCUMENTS

| | | |
|---|---|---|
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,300,891 B2 | 10/2012 | Chen et al. |
| 8,369,608 B2 | 2/2013 | Gunaratne |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 8,738,523 B1 | 5/2014 | Sanchez et al. |
| 8,947,217 B2 | 2/2015 | Moussa et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0011399 A1* | 1/2006 | Brockway ............ B60T 17/18 180/272 |
| 2006/0019224 A1 | 1/2006 | Behar et al. |
| 2006/0143647 A1 | 6/2006 | Bill |
| 2006/0149428 A1 | 7/2006 | Kim et al. |
| 2006/0170945 A1 | 8/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0193344 A1 | 7/2009 | Smyers |
| 2009/0209829 A1 | 8/2009 | Yanagidaira et al. |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Foebes et al. |
| 2009/0285456 A1 | 11/2009 | Moon et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0134302 A1 | 6/2010 | Ahn et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0083075 A1* | 4/2011 | MacNeille ............ G10L 15/22 715/728 |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0257985 A1* | 10/2011 | Goldstein ............ G06F 16/5838 705/1.1 |
| 2011/0263946 A1 | 10/2011 | el Kaliouby et al. |
| 2012/0109452 A1 | 5/2012 | Autran et al. |
| 2012/0150430 A1 | 6/2012 | French et al. |
| 2012/0324491 A1 | 12/2012 | Bathiche et al. |
| 2013/0023337 A1 | 1/2013 | Bowers et al. |
| 2013/0116587 A1 | 5/2013 | Sommo et al. |
| 2013/0197409 A1 | 8/2013 | Baxter et al. |
| 2013/0204455 A1 | 8/2013 | Chia et al. |
| 2014/0171752 A1 | 6/2014 | Park et al. |
| 2014/0172910 A1 | 6/2014 | Jung et al. |
| 2014/0218187 A1 | 8/2014 | Chun et al. |
| 2015/0258995 A1 | 9/2015 | Essers et al. |
| 2016/0104486 A1 | 4/2016 | Penilla et al. |
| 2017/0003784 A1 | 1/2017 | Garg et al. |
| 2019/0176837 A1 | 6/2019 | Williams et al. |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

Matsugu, M., Mori, K., Mitari, Y., & Kaneda, Y. (2003). Subject independent facial expression recognition with robust face detection using a convolutional neural network. Neural Networks, 16(5-6), 555-559.

Rana Ayman El Kaliouby, Mind-reading machines: automated inference of complex mental states, Jul. 2005, University of Cambridge, Cambridge, United Kingdom.

(56) References Cited

OTHER PUBLICATIONS

International Search Report dated Nov. 14, 2011 for PCT/US2011/39282.
International Search Report dated Apr. 16, 2012 for PCT/US2011/054125.
International Search Report dated May 24, 2012 for PCT/US2011/060900.
Xiaoyu Wang, An HOG-LBP human detector with partial occlusion handling, Sep. 29, 2009, IEEE 12th International Conference on Computer Vision, Kyoto, Japan.
Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.
Nicholas R. Howe and Amanda Ricketson, Improving the Boosted Correlogram, 2004, Lecture Notes in Computer Science, ISSN 0302-9743, Springer-Verlag, Germany.
Xuming He, et al., Learning and Incorporating Top-Down Cues in Image Segmentation, 2006, Lecture Notes in Computer Science, ISBN 978-3-540-33832-1, Springer-Verlag, Germany.
Ross Eaton, et al., Rapid Training of Image Classifiers through Adaptive, Multi-frame Sampling Methods, Oct. 2008, IEEE 37th Applied Imagery Pattern Recognition Workshop, Washington DC.
Verkruysse, Wim, Lars O. Svaasand, and J. Stuart Nelson. "Remote plethysmographic imaging using ambient light." Optics express 16.26 (2008): 21434-21445.
Albiol, Alberto, et al. "Face recognition using HOG—EBGM." Pattern Recognition Letters 29.10 (2008): 1537-1543.

\* cited by examiner

VEHICLE MANIPULATION USING COGNITIVE STATE ENGINEERING

RELATED APPLICATIONS

This application claims the benefit of U.S. provisional patent applications "Vehicle Manipulation Using Cognitive State Engineering" Ser. No. 62/679,825, filed Jun. 3, 2018, and "Image Analysis for Human Perception Artificial Intelligence" Ser. No. 62/827,088, filed Mar. 31, 2019.

This application is also a continuation-in-part of U.S. patent application "Vehicle Manipulation using Occupant Image Analysis" Ser. No. 15/875,644, filed Jan. 19, 2018, which claims the benefit of U.S. provisional patent applications "Vehicle Manipulation using Occupant Image Analysis" Ser. No. 62/448,448, filed Jan. 20, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, "Image Analysis for Emotional Metric Generation" Ser. No. 62/524,606, filed Jun. 25, 2017, "Image Analysis and Representation for Emotional Metric Threshold Evaluation" Ser. No. 62/541,847, filed Aug. 7, 2017, "Multimodal Machine Learning for Emotion Metrics" Ser. No. 62/557,460, filed Sep. 12, 2017, "Speech Analysis for Cross-Language Mental State Identification" Ser. No. 62/593,449, filed Dec. 1, 2017, "Avatar Image Animation using Translation Vectors" Ser. No. 62/593,440, filed Dec. 1, 2017, and "Directed Control Transfer for Autonomous Vehicles" Ser. No. 62/611,780, filed Dec. 29, 2017.

The patent application "Vehicle Manipulation using Occupant Image Analysis" Ser. No. 15/875,644, filed Jan. 19, 2018, is also a continuation-in-part of U.S. patent application "Image Analysis in Support of Robotic Manipulation" Ser. No. 15/273,765, filed Sep. 23, 2016, which claims the benefit of U.S. provisional patent applications "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 12, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Image Analysis in Support of Robotic Manipulation" Ser. No. 15/273,765, filed Sep. 23, 2016 is a continuation-in-part of U.S. patent application "Mental State Event Definition Generation" Ser. No. 14/796,419, filed Jul. 10, 2015 which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF INVENTION

This application relates generally to vehicle manipulation and more particularly to vehicle manipulation using cognitive state engineering.

BACKGROUND

A wide variety cognitive states, moods, and emotions are experienced while people travel because transportation routinely presents travelers with situations that can be physically, mentally, and emotionally challenging. Travel situations include being stuck in gridlocked traffic, waiting in endless security check lines that appear never to move, and many others. Despite these situations, the individuals travel from one location to another for financial reasons such as commuting to and from work or school; for personal reasons such as vacation, recovery, relaxation, or adventure; or for exercise, to name only a few. For other individuals, travel is undesirable. These unwilling travelers may be fleeing from war, famine, natural or environmental disasters, or may be victims of economic displacement. Transportation modes include ground transportation, water transportation, and air transportation. The transportation modes are chosen by travelers based on convenience, availability, and/or cost. Transportation modes further depend on the purpose of the travel such as getting across town or hauling goods. Other modes of transportation, such as space transportation, may be available in the near future.

Whichever transportation mode is chosen, people spend a substantial amount of time traveling. Travel-related activities including getting to, waiting for, traveling in, or parking the vehicle; waiting in security lines to get on the vehicle; among many others, all take time. Traveling is time consuming at its best, and loathsome, frustrating, irritating, and stressful at its worst. Some travelers use public transportation networks, such as buses, trains, and airplanes; ride-sharing services such as Uber™ and Lyft™; personal vehicles; and car sharing services such as Zipcar™; to travel among various destinations. Travel times include daily commutes to and from the office; taking the kids to school, soccer practice, and piano lessons; taking the pets to the veterinary; shopping; running errands; traveling for business or vacation; and the many other common activities that require transportation. Individuals meet their transportation needs by using a variety of vehicles. The choice of vehicles available most often depends on where people live. The vehicles can include cars and motorcycles; buses, trains and subways; ride and ride sharing services; and even unmotorized vehicles such as bicycles, skateboards, or scooters. The time spent on travel is time lost from productive or meaningful activities such as work, study, artistic pursuits, being with family or friends, and so on. Rush hour traffic, accidents, and poorly maintained roads greatly complicate and interfere with vehicle transportation. The difficulties of transportation are further exacerbated by operating an unfamiliar vehicle, traveling in an unfamiliar city, and even in some situations having to remember to operate a vehicle on the opposite side of the road. Catastrophic consequences can result from failure to remain alert to these transportation realities. Irritated or belligerent vehicle operators can experience road rage and other antisocial behaviors, while bored, impaired, sleepy, distracted, or inattentive drivers can cause vehicular accidents resulting in injury to themselves or other vehicle occupants, pedestrians, bicyclists, or animals, and damage to property.

Transportation systems are complex. Transportation in general, and specifically urban transportation, presents labyrinthine and difficult design, financial, and management problems, any of which can directly impact travelers. Overly congested highways and surface roads, and chronically insufficient parking, each directly influence the cognitive or mental states, moods, and emotions of travelers. The congested roadways cause significantly longer and more dangerous commutes, while the lack of available parking increases the amount of time wasted looking for a place to leave a vehicle safely. Public transportation, if at all available to the traveler at her particular location, presents challenges of its own. The challenges include overfilled buses, trains, and subways during commuting hours; underused routes due to poor planning or a general lack of interest, and other factors. The increased use of bicycles or scooters through sharing services presents other, further challenges. Challenging or dangerous situations arise when vehicles, bicycles, or scooters share overfilled roadways that were not originally or mindfully designed for multi-use scenarios. Although vehicle operators and occupants may not be directly involved in the management and financing of transportation systems, those travelers directly suffer from and experience the frustration and annoyance of using the transportation systems, all while carrying the tax burden of paying to construct, maintain, operate, and upgrade those systems.

SUMMARY

Vehicular manipulation in disclosed techniques uses cognitive state engineering based on analysis of images and other data of a vehicle occupant. The vehicle to be manipulated can be an autonomous vehicle, a semi-autonomous vehicle, and so on. An in-vehicle imaging device is used to collect images of a vehicle occupant, where the images include facial data. The vehicle can be a first vehicle, a second vehicle, a third vehicle, a public transportation vehicle, etc. The images can include images based on various light spectra such as visible light images or near-infrared (NIR) images. Other in-vehicle sensors can include a microphone for collecting audio data or voice data, and other sensors to collect physiological data. A computing device is used to analyze the one or more images to determine a cognitive state. The computing device can be a device within the vehicle, an electronic device used by an occupant of the vehicle, a computing device such as a server beyond the vehicle, and the like. The cognitive state is mapped to a loading curve, where the loading curve represents a continuous spectrum of cognitive state loading variation. The loading curve can include a range or degree of cognitive states, where the curve can run from cognitive "underload" to cognitive overload. Cognitive underload can include lassitude, ennui, inattention, etc., while cognitive overload can include distraction, capitulation, and the like. The vehicle is manipulated, based on the mapping to the loading curve, where the manipulating is accomplished using cognitive state alteration engineering. Cognitive state alteration engineering can use various techniques to calm a driver experiencing a degree of cognitive overload, or to stimulate a driver experiencing a degree of cognitive underload. Cognitive state alteration engineering seeks to move or shift the cognitive state of the individual to an optimal cognitive state range.

In embodiments, a computer-implemented method for vehicle manipulation comprises: obtaining one or more images of a vehicle occupant using one or more imaging devices within a vehicle, wherein the one or more images include facial data of the vehicle occupant; analyzing, using a computing device, the one or more images to determine a cognitive state; mapping the cognitive state to a loading curve, wherein the loading curve represents a continuous spectrum of cognitive state loading variation; and manipulating the vehicle, based on the mapping to the loading curve, wherein the manipulating is accomplished using cognitive state alteration engineering. Some embodiments comprise obtaining additional images of one or more additional occupants of the vehicle, wherein the additional images are analyzed to determine one or more additional cognitive states. Other embodiments include adjusting the mapping the cognitive state, wherein the adjusting is performed using the additional cognitive states and changing the manipulating the vehicle based on the adjusting. In embodiments, the analyzing is performed beyond eye region input from the one or more images.

In some embodiments, the method further includes obtaining audio information from the occupant of the vehicle and augmenting the analyzing based on the audio information. The audio information can include speech, non-speech vocalizations, and so on. The non-speech vocalizations can include grunts, yelps, squeals, snoring, sighs, laughter, filled pauses, unfilled pauses, or yawns. Further embodiments include obtaining physiological information from the occupant of the vehicle and augmenting the analyzing based on the physiological information. The physiological information can include heart rate, heart rate variability, respiration rate, skin conductivity, and so on. The occupant of the vehicle can be a driver or operator of the vehicle or can be a passenger within the vehicle. The vehicle can be an autonomous vehicle or a semi-autonomous vehicle. In embodiments, the method includes rendering the cognitive state on a display located within the vehicle. The rendering the information can include showing the information on an in-dashboard display, an in-vehicle display, a heads-up display, an electronic device such as a smartphone associated with the vehicle occupant, etc.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

Figure 1:
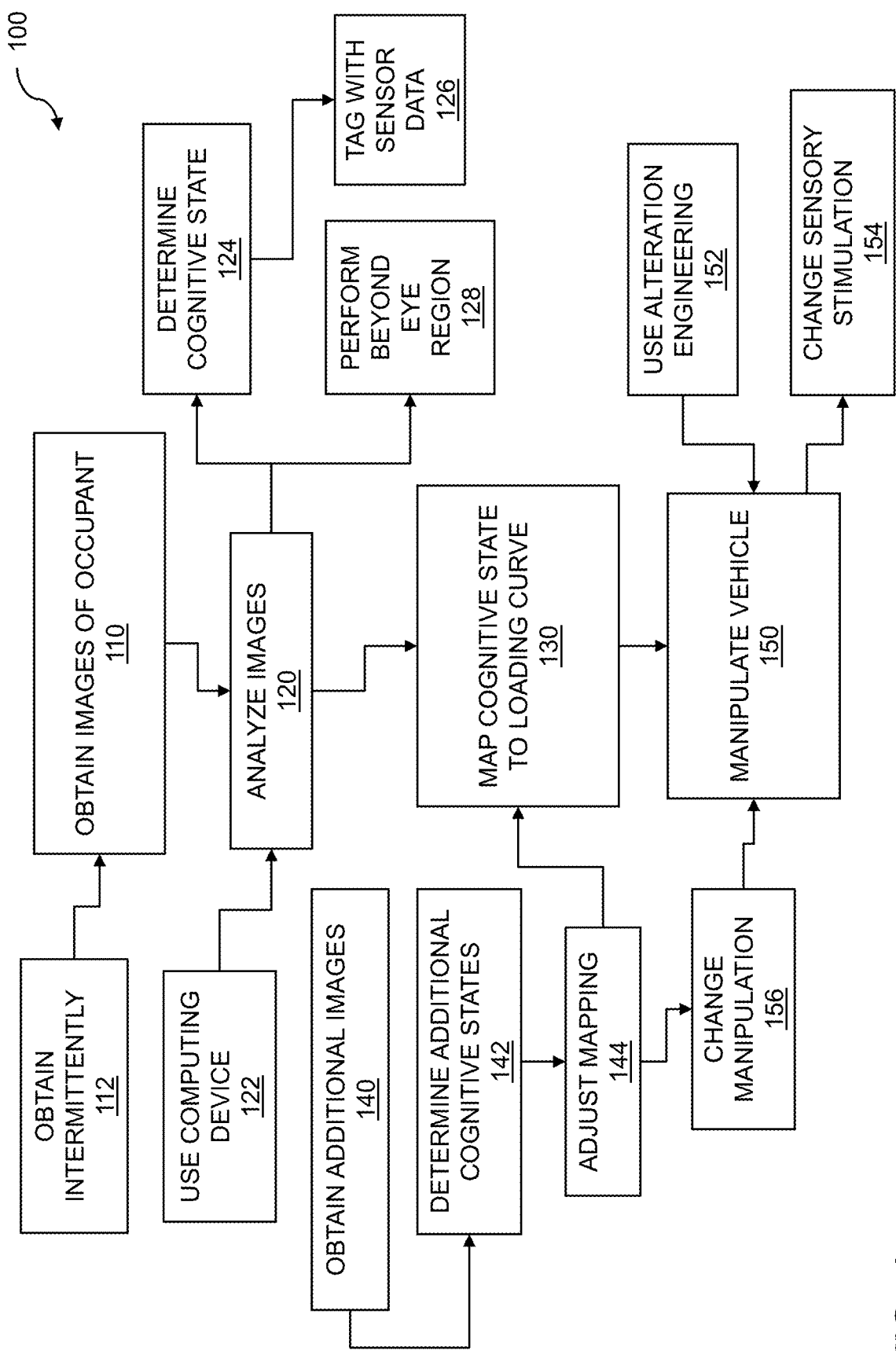
FIG. 1 is a flow diagram for vehicle manipulation using cognitive state engineering.

Many individuals, whether they live in urban, suburban, or rural areas, spend hundreds of hours or more per year traveling in vehicles. The vehicles that are typically used for travel include public, private, or commercial vehicles such as buses, trains, airplanes, automobiles, ride share vehicles, and so on. The hours that individuals are spending in vehicles include commuting to and from work, running errands, meeting appointments, traveling, etc. An individual who is traveling within or atop a vehicle can experience a wide range of cognitive states. The individual's cognitive states can be determined by analyzing cognitive state data that can be collected from the individual. The cognitive state data can include image data, facial data, audio data, voice data, speech data, non-speech vocalizations, physiological data, and the like. The analysis of the cognitive state data for the vehicle occupant can be used to manipulate the vehicle.

The vehicle manipulation can be provided to authorize a person to access or operate a vehicle, to configure the vehicle based on preferences of a vehicle occupant, to control or operate an autonomous or semi-autonomous vehicle, and so on. The vehicle manipulation can include directing a vehicle along a vehicle travel route that is best suited to the cognitive state of the vehicle occupant. The vehicle travel route can be manipulated based on a route ranking of "low stress", "beautiful", "happy", and so on. More important, vehicle manipulation can include using cognitive state alteration engineering. Cognitive state alteration engineering can be used to calm a driver experiencing a degree of cognitive overload or to stimulate a driver experiencing a degree of cognitive "underload". Cognitive underload can include a degree of boredom, ennui, etc. Cognitive state alteration engineering seeks to shift the cognitive state of a vehicle occupant to an optimal state in order to improve driver satisfaction, to reduce travel hazards, etc.

Other determinations can be made based on vehicle occupant's cognitive state. The determinations can include whether the occupant is in a fit cognitive state to operate the vehicle safely (e.g. not impaired); should take a break from operating or traveling in the vehicle during long trips; should seek an alternative travel route due to weather, accident, or construction; and so on. The determinations of cognitive states and the vehicle manipulations directly benefit vehicle operator or passenger convenience and comfort, improve road safety, enhance transportation experiences, etc. Further, collecting cognitive state data enables manipulation of vehicle operating characteristics and vehicle environmental experiences for the operators and passengers. The vehicle in which the vehicle occupant or occupants are traveling can be an autonomous vehicle, a semi-autonomous vehicle, etc. The benefits of manipulating an autonomous vehicle or a semi-autonomous vehicle range from reducing the time required to configure a vehicle to an individual to verifying that the individual is in a cognitive state capable of operating the vehicle, is permitted to operate the vehicle, etc. The enhanced transportation experience for the individual includes autonomous operation, security, or comfort. The road safety improvements are derived from manipulating the vehicle on behalf of the individual include safer vehicle operations when navigating in foreign surroundings or operating an unfamiliar vehicle, and are further derived from preventing a sleepy, impaired, or inattentive individual from operating the vehicle.

In the disclosed techniques, vehicle manipulation, where the vehicles can include semi-autonomous vehicles or autonomous vehicles, uses cognitive state engineering. Vehicle manipulation can be performed for a variety of purposes including adjusting the cognitive state of a vehicle occupant, assisting an occupant of the vehicle, permitting access to a vehicle, configuring the vehicle based on preferences of the vehicle occupant, and so on. The vehicle manipulation can also include choosing routes for the vehicle based on a vehicle route mood map, improving comfort of the occupant, reducing stress and other negative cognitive states, and so on. The vehicle manipulation uses image-based analysis. Images of a vehicle occupant are obtained using one or more imaging devices within a vehicle. The imaging devices can include cameras, where the cameras can include a video camera, a still camera, a camera array, a plenoptic camera, a web-enabled camera, a visible light camera, a near-infrared (NIR) camera, a heat camera, and so on. The obtained images include facial data of the vehicle occupant. A computing device is used to analyze the one or more images to determine a cognitive state. The computing device can include an on-board computer, an electronic device used by the vehicle occupant, a server located beyond the vehicle, etc. The cognitive states can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The cognitive state can be mapped to a loading curve, where the loading curve can represent a continuous spectrum of cognitive state loading variation. The cognitive state loading variation can range from cognitive underload to cognitive overload. The loading curve can include a bell curve function. In embodiments, the bell curve function can represent a Yerkes-Dodson law curve. The vehicle can be manipulated, based on the mapping to the loading curve, where the manipulating can be accomplished using cognitive state alteration engineering. The cognitive state can be rendered on a display located within the vehicle.

FIG. 1 is a flow diagram for vehicle manipulation using cognitive state engineering. Vehicle manipulation uses cognitive state engineering. Images include facial data of a vehicle occupant. The images are analyzed using a computing device to determine a cognitive state. The cognitive state is mapped to a loading curve, where the loading curve represents cognitive state loading variation. The vehicle is manipulated based on the mapping to the loading curve. The manipulating is accomplished using cognitive state alteration engineering. In some embodiments, vehicle manipulation can simply include observing or monitoring an occupant or driver within a vehicle.

The flow 100 includes obtaining one or more images of a vehicle occupant 110 using one or more imaging devices within a vehicle. The one or more images that are obtained include facial data of the vehicle occupant. The images can include one or more light spectra such as visible light, near-infrared light, and so on. The one or more imaging devices within the vehicle can include any of a variety of cameras or other image capture devices suitable for image-based analysis. A camera can include a webcam, a video camera, a still camera, a thermal imager, a near infrared (NIR) camera, a CCD device, a phone camera, a three-dimensional camera, a depth camera, a light field camera, multiple webcams used to show different views of a person, or any image capture device. A camera or image capture device can capture light of various wavelengths. In embodiments, a wavelength of the near infrared light can be less than 950 nm. Other types of data of a vehicle occupant can be collected. In some embodiments, audio information is collected in place of images or in addition to images to augment the cognitive state data contained therein. Further data types of the vehicle occupant may be collected. In embodiments, physiological information from the occupant of the vehicle is collected in place of images or audio information, or in addition the images or audio information. The physiological data can be used to augment the analyzing. The vehicle occupant can be the driver of the vehicle, the operator of the vehicle, a passenger of the vehicle, etc. The vehicle can be an automobile, a bus, a van, a truck, a train, an airplane, a ship, etc. Other embodiments include intermittent obtaining of images 112 that include facial data. The intermittent obtaining of images can occur when a vehicle occupant is facing an imaging device, or not when the vehicle occupant is facing away from the imaging device.

The flow 100 includes analyzing 120 the one or more images. The analyzing includes using a computing device 122. The computing device can include a computing device within the vehicle; a smartphone, a personal digital assistant (PDA), a tablet computer, a laptop computer, etc., associated with the vehicle occupant; a server located within the vehicle; a computing device located beyond the vehicle; etc. A computing device located beyond the vehicle can include a server, a remote server, a blade server, a cloud-based server, a mesh server, or the like. The analyzing the images includes determining a cognitive state 124. One or more cognitive states can be determined based on the analyzing. In embodiments, the cognitive state can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Further to analyzing the cognitive state data, the cognitive state data can be tagged. Further embodiments include tagging the cognitive state data with sensor data 126. The tagging the cognitive state data can be based on other data that may be collected relating to a vehicle, the exterior of the vehicle, the interior of the vehicle, and so on. In embodiments, the sensor data can include one or more of vehicle temperature, outside temperature, time of day, level of daylight, weather conditions, headlight activation, windshield wiper activation, entertainment center selection, entertainment center volume, etc. The analyzing of the one or more images including facial data can include analyzing a face, regions of a face, and so on. In embodiments, the analyzing is performed beyond eye region 128 input from the one or more images.

The flow 100 includes mapping the cognitive state to a loading curve 130, where the loading curve represents a continuous spectrum of cognitive state loading variation. Cognitive load in this context can refer to an amount of effort expended by an occupant of a vehicle to process tasks related to operating, traveling in, or traveling atop the vehicle. The expended effort can relate to holding data in a small memory for processing. The data can be held in a temporary, "working", or short-term memory. Cognitive load can indicate a level of engagement, distraction, inattention, etc., of the vehicle occupant as she or he deals with tasks related to the vehicle. Cognitive load can be adjusted for vehicle manipulation using cognitive state engineering. The vehicle occupant, whether an operator, driver, passenger, etc., can experience a variety of cognitive states. The occupant can experience one or more cognitive states. The cognitive states experienced by the occupant can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth, etc. Cognitive load relates to the cognitive states based on the mapping to the loading curve. The loading curve can represent a continuous spectrum of cognitive state loading variation from a low cognitive state loading to a high cognitive state loading. The spectrum can range widely. In embodiments, the spectrum of cognitive state loading variation can include a range from very underloaded to very overloaded. Various continuous curves can describe the spectrum of cognitive state loading variation. In embodiments, the spectrum of cognitive state loading variation comprises a bell curve function. Other curves can be used to describe the loading variation. In embodiments, the bell curve function represents a Yerkes-Dodson law curve. The Yerkes-Dobson law can include an empirical relationship between physiological arousal (attentive, alerts, awake, etc.) and performance, which here can refer to driver performance. Adjusting the cognitive load of the vehicle occupant using cognitive state engineering can improve vehicle operation safety, enhance the experience of the vehicle occupant, and the like.

The flow 100 includes obtaining additional images 140 of one or more additional occupants of the vehicle. The additional images can be obtained intermittently. The intermittent obtaining of the images can occur when an occupant of the vehicle is facing in the direction of an image capture device, may be obtained periodically based on an amount of time, and so on. The additional images can be obtained using image capture devices mentioned previously, or can be obtained by other image capture devices within the vehicle or image capture devices beyond the vehicle. In the flow 100, the additional images are analyzed to determine one or more additional cognitive states 142. The additional cognitive states can be used for a variety of purposes such as mapping to cognitive loads. Embodiments include adjusting the mapping of the cognitive state, where the adjusting is performed using the additional cognitive states 144. The adjusting the mapping can be based on the role of the occupant of the vehicle, such as vehicle operator as opposed to vehicle passenger, based on interactions between or among vehicle occupants, etc.

The flow 100 includes manipulating the vehicle 150 based on the mapping to the loading curve. The vehicle that is manipulated can include an autonomous vehicle, a semi-autonomous vehicle, and so on. The manipulating the vehicle can include a variety of operations such as a locking out operation of the vehicle to prevent unauthorized use or to prevent an impaired driver from operating the vehicle. The manipulating the vehicle can include making recommendations to the vehicle operator such as taking a break, seeking an alternate route, and the like. The manipulating the vehicle can include brake activation, throttle control, steering control, vehicle route navigation, etc. The manipulating the vehicle can be based on convenience, needs, preferences, and so on, of a vehicle operator or vehicle passenger. Such manipulation of the vehicle can include adjusting vehicle seats, where the adjusting can include moving the seat up or down, forward or backward; adjusting seat tilt; adjusting seat temperature; etc. The manipulating the vehicle can include adjusting the climate within the vehicle. The climate within the vehicle can be controlled based on the occupant of the vehicle, time of day, season of year (e.g. heat or air conditioning), and so on.

In the flow 100, the manipulating is accomplished using cognitive state alteration engineering 152. The cognitive state alteration engineering can be used to increase or decrease cognitive load of a vehicle occupant to attain optimum performance based on an optimum cognitive load. The vehicle occupant can include the vehicle operator, driver, passenger, or other person within or atop the vehicle. Adjusting cognitive load can include increasing cognitive load, decreasing cognitive load, etc. For low cognitive load, various stimuli can be provided to the driver in order to engage the driver. In embodiments, the manipulating includes changing vehicle occupant sensory stimulation 154.

Various changes of sensory stimulation can be performed based on types of stimulation. In embodiments, the sensory stimulation includes aural, visual, or haptic stimulation. The stimuli can include displaying a message on a screen, displaying more screens, providing an audio alert, changing audio content or volume such as changing the radio or streaming channel, providing a haptic alert such as a buzzing vehicle seat or steering wheel, and so on. For high cognitive load, where the driver can already be overwhelmed by external stimuli, fewer stimuli can be provided to the driver. Providing fewer stimuli can include displaying fewer screens, less visual information, or fewer alerts; reducing audio stimuli such as switching to a calmer audio source or lowering the volume; and the like. The visual, audio, or haptic stimuli can be manipulated based on a cognitive state profile of the occupant of the vehicle. Further embodiments include changing the manipulating of the vehicle based on the adjusting 156, where the adjusting is based on the additional images that were obtained. The adjusting can also be based on additional audio information, physiological information, and so on. Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
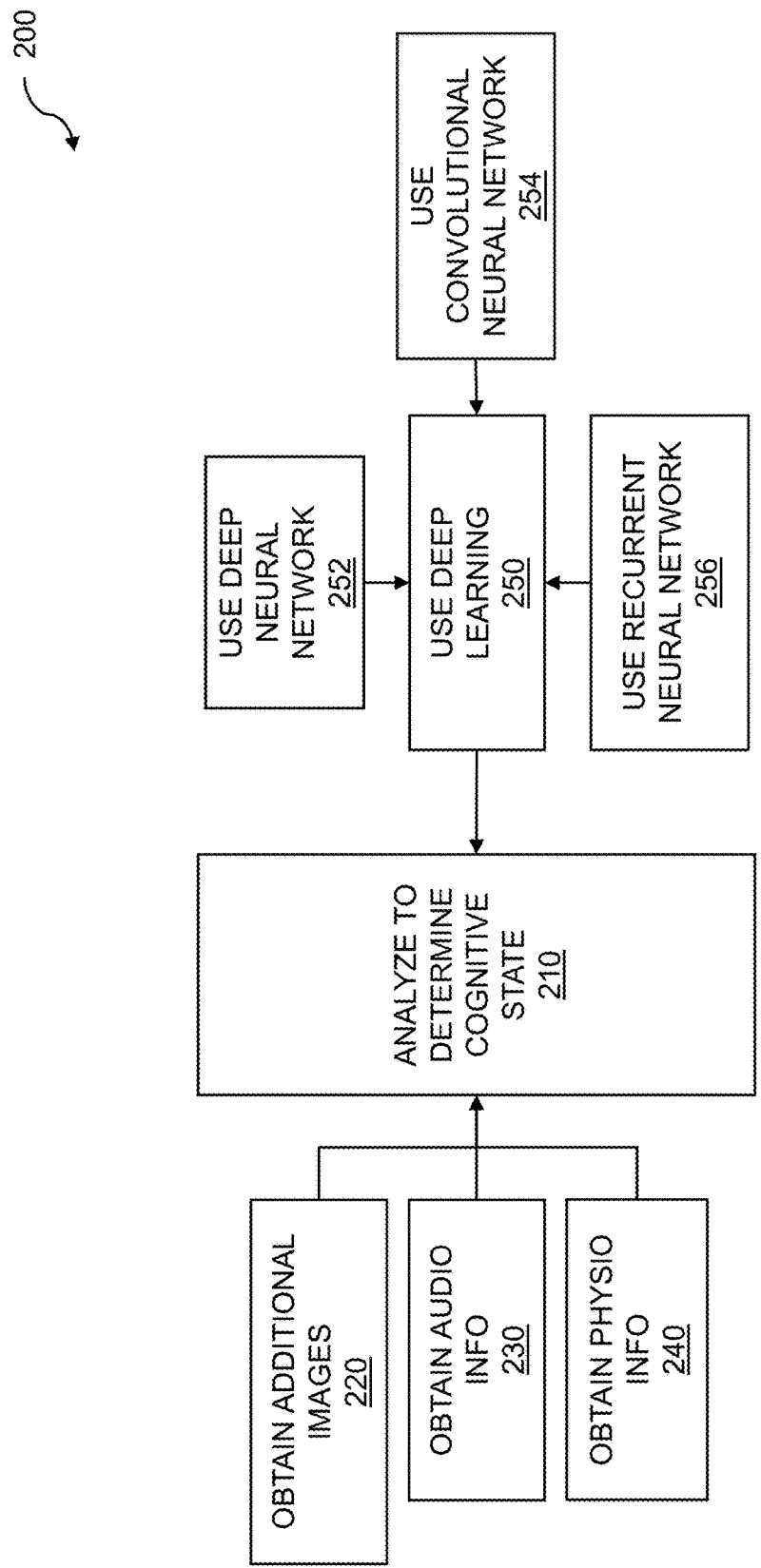
FIG. 2 is a flow diagram for further cognitive state analysis.

FIG. 2 is a flow diagram for further cognitive state analysis. Additional cognitive state data such as images, audio information, physiological information, and so on, can be obtained and analyzed to determine a cognitive state. The further cognitive state analysis supports vehicle manipulation using cognitive state engineering. The cognitive state or states can be mapped to a loading curve, and the vehicle can be manipulated based on the mapping. The manipulation is accomplished using cognitive state alteration engineering. The flow 200 includes analyzing, using a computing device, additional cognitive state data to determine a cognitive state. The computing device can include an on-vehicle computing device, an electronic device such as a smartphone or tablet computer associated with the vehicle occupant, and so on. The computing device can include a computing device located beyond the vehicle, where the computing device can include a computing device in another vehicle, a server, a blade server, a cloud server, a mesh server, and the like.

The flow 200 includes obtaining additional images 220 of one or more additional occupants of the vehicle, where the additional images are analyzed 210 to determine one or more additional cognitive states. Images of the one or more additional occupants of the vehicle can be obtained using imaging devices within a vehicle. The images can include visible light images, near-infrared images, or images comprising other spectra, where the images of any type include facial data. The flow 200 includes obtaining audio information 230 from the occupant of the vehicle and augmenting the analyzing based on the audio information. The audio information can be obtained using a microphone, audio transducer, etc., where the microphone, for example, can be an in-vehicle microphone, a microphone coupled to an electronic device associated with a vehicle occupant, etc. The microphone can obtain a variety of audio information such as in-vehicle sounds; exterior sounds such as road noise, wind noise, or traffic noise; etc. In embodiments, the audio information can include speech. The speech information can include speech from the occupant of the vehicle, speech detected in an audio source such as a radio or streaming station, and the like. In other embodiments, the audio information can include non-speech vocalizations. The non-speech vocalizations can include a variety of human generated sounds. In embodiments, the non-speech vocalizations can include grunts, yelps, squeals, snoring, sighs, laughter, filled pauses, unfilled pauses, or yawns. The flow 200 includes obtaining physiological information 240 from the occupant of the vehicle and augmenting the analyzing based on the physiological information. The physiological information can be inferred from image data or audio data, collected using sensors, and so on. The physiological information can include heart rate, heart rate variability, respiration rate, skin conductivity, and the like.

The flow 200 includes analyzing, where the analyzing is performed using deep learning 250. Deep learning can be based on learning one or more representations related to data, rather than relying on algorithms that can be specific to a given data analysis task. Data representations, such as those based on feature learning, include techniques for automating the discovery, by a deep learning system, of representations that can be used to classify or detect features in raw data. In embodiments, the learning is performed using a deep neural network 252. A deep neural network can include an input layer, an output layer, and hidden layers internal to the neural network. A deep learning network can use weights, biases, and layers that can be learned as part of training the deep neural network. A deep neural network can include a feed-forward network, in which data such as training data or raw data can flow from an input layer, through the neural network, to an output layer. In other embodiments, the learning is performed using a convolutional neural network (CNN) 254. A convolutional neural network can include properties such as space invariance, shift invariance, or translation invariance, which are particularly useful properties for image analysis. A CNN can require little preprocessing of input data because the CNN can learn filters. The learning the filters can obviate the need to code the filters. The filters can enhance image classification tasks such as facial data analysis. In further embodiments, the learning is performed using a recurrent neural network 256. A recurrent neural network (RNN) can include connections between nodes to form a directed graph. The directed graph can be along a sequence. An RNN can exhibit temporal behavior by using storage internal to the RNN to process input data sequences. Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors.

Figure 3:
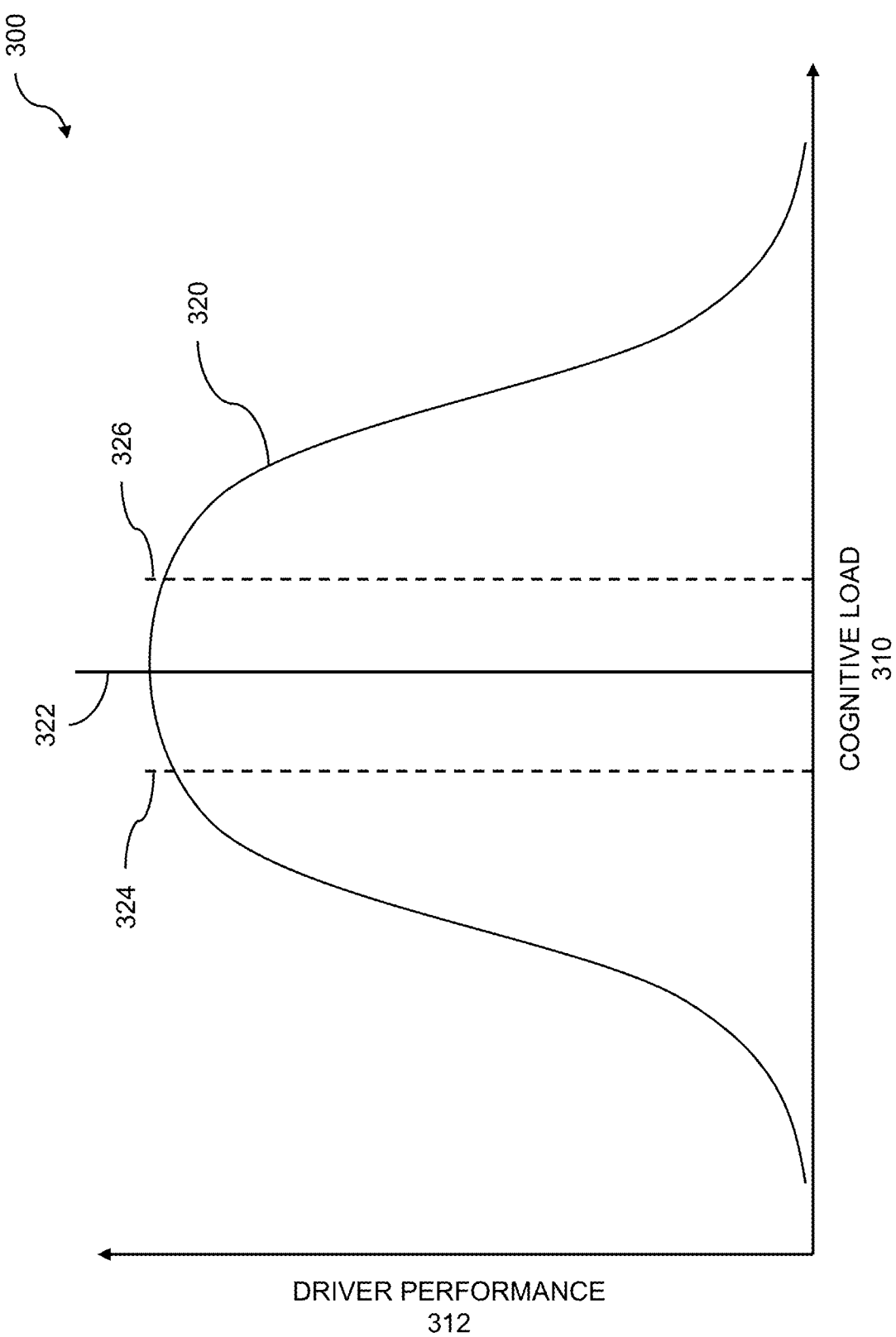
FIG. 3 shows a curve for driver performance versus cognitive load.

FIG. 3 shows a curve for driver performance versus cognitive load. Cognitive load can include an amount of cognitive effort required by a vehicle occupant as the occupant travels within or atop the vehicle. Cognitive load can indicate how engaged, distracted, inattentive, etc., the vehicle occupant can be with tasks related to the vehicle. Cognitive load can be adjusted for vehicle manipulation using cognitive state engineering. A vehicle occupant who is operating the vehicle or traveling in the vehicle can experience a variety of cognitive states. The cognitive states experienced by the occupant can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. In addition to one or more cognitive states, the occupant can experience cognitive load. Cognitive load can include an amount of cognitive effort required of the occupant to perform various tasks within the vehicle. The tasks can include operating the vehicle, listening to audio, negotiating a travel route, maneuvering in traffic, and the like. The cognitive load can be determined by mapping a cognitive state to a loading curve. The loading curve can represent a continuous spectrum of cognitive state loading variation. The spectrum of cognitive state loading variation can include a range from very underloaded to very overloaded. Adjusting the cognitive load of the vehicle occupant using cognitive state engineering can improve vehicle operation safety, enhance the experience of the vehicle occupant, and the like.

A curve for driver performance 312 versus cognitive load 310 is shown 300. The curve 320 can represent a bell curve function or other continuous curve. In embodiments, the bell curve function can represent a Yerkes-Dodson law curve. The Yerkes-Dodson law can include an empirical relationship between physiological arousal (attentive, alert, awake, etc.) and performance, which here can refer to driver performance. The curve function can be used to determine that for a low cognitive load value, driver performance can be low. For low cognitive load, or cognitive "underload", the driver can be inattentive due to the dull nature of operating or traveling in the vehicle, can be distracted, bored, disengaged, and so on. For high cognitive load, or cognitive overload, the driver can be unable to handle the tasks associated with operating or traveling in the vehicle. Cognitive overload can include distraction, but in this latter case, the distraction can be due to a superfluity of stimuli, operating tasks, etc., occurring simultaneously. Between cognitive underload and cognitive overload is an optimum value 322 or range of values 324 and 326. The optimum value or range of values can show a cognitive load or range of cognitive loads over which driver performance can be maximized. At the optimal value or within the range of values, the driver is able to handle the tasks associated with the vehicle while remaining alert, attentive, engaged, and so on.

The cognitive state alteration engineering can be used to increase or decrease cognitive load to attain optimum driver performance. For low cognitive load, various stimuli can be provided to the driver in order to engage the driver. The stimuli can include displaying a message on a screen, displaying more screens, providing an audio alert, changing audio content such as changing the radio or streaming channel, providing a haptic alert such as a buzzing vehicle seat, and so on. For high cognitive load, where the driver can already be overwhelmed by external stimuli, fewer stimuli can be provided to the driver. Providing fewer stimuli can include displaying fewer screens, less visual information, or fewer alerts; reducing audio stimuli such as switching to a calmer audio source; and the like.

Figure 4:
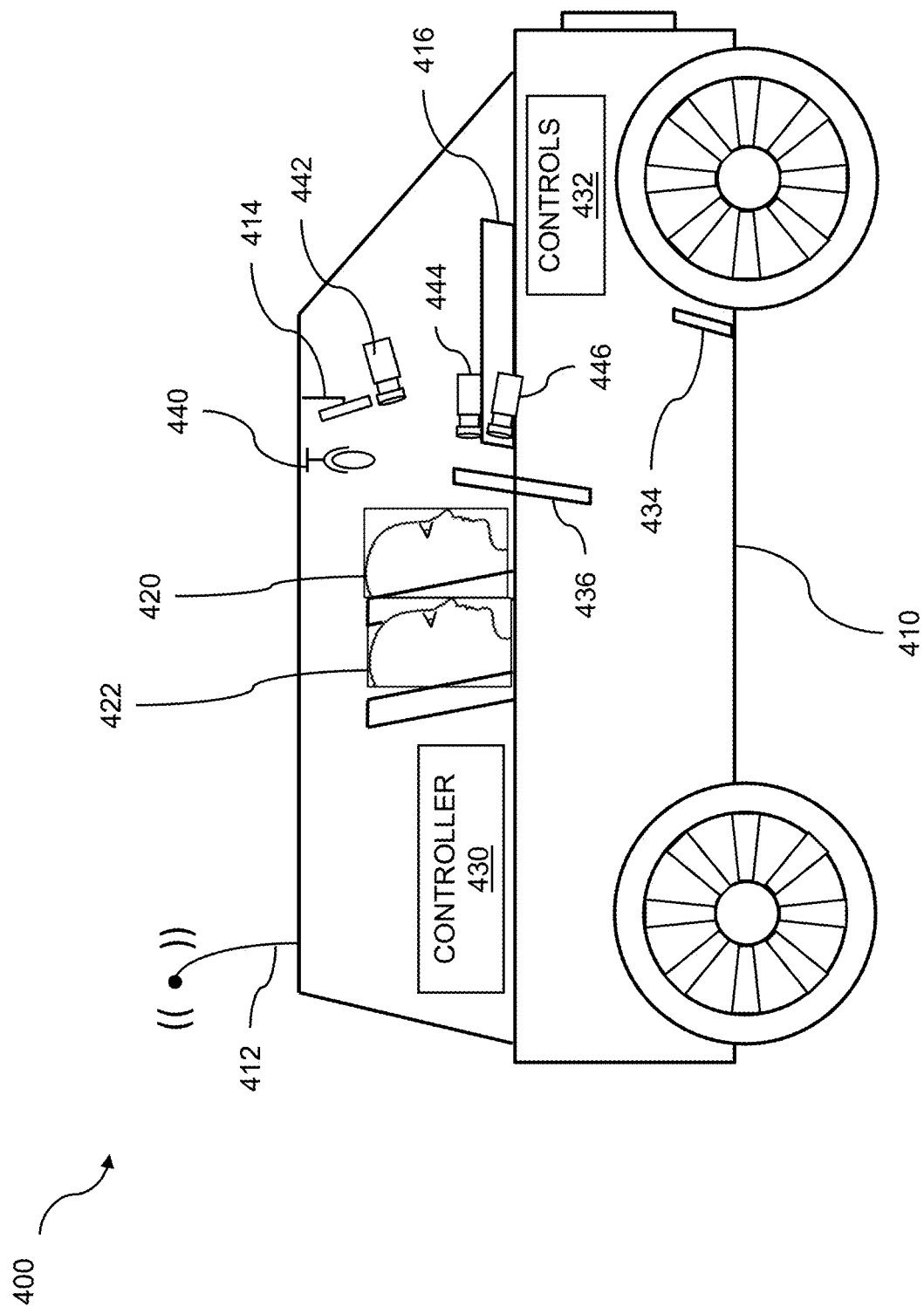
FIG. 4 is a system diagram for an interior of a vehicle.

FIG. 4 is a system diagram for an interior of a vehicle 400. Vehicle manipulation can be based on cognitive state engineering. Images including facial data of a vehicle occupant are obtained using one or more imaging devices within a vehicle. The images are analyzed to determine cognitive state. The cognitive state is mapped to a loading curve representing a continuous spectrum of cognitive state loading variation. The vehicle is manipulated using cognitive state alteration engineering. One or more occupants of a vehicle 410, such as occupants 420 and 422, can be observed using a microphone 440, one or more cameras 442, 444, or 446, and other audio and image capture techniques. The image data can include video data. The video data and the audio data can include cognitive state data, where the cognitive state data can include facial data, voice data, physiological data, and the like. The occupant can be a driver 420 of the vehicle 410, a passenger 422 within the vehicle, and so on.

The cameras or imaging devices that can be used to obtain images including facial data from the occupants of the vehicle 410 can be positioned to capture the face of the vehicle operator, the face of a vehicle passenger, multiple views of the faces of occupants of the vehicle, and so on. The cameras can be located near a rear-view mirror 414 such as camera 442, positioned near or on a dashboard 416 such as camera 444, positioned within the dashboard such as camera 446, and so on. The microphone 440, or audio capture device, can be positioned within the vehicle such that voice data, speech data, non-speech vocalizations, and so on, can be easily collected with minimal background noise. In embodiments, additional cameras, imaging devices, microphones, audio capture devices, and so on, can be located throughout the vehicle. In further embodiments, each occupant of the vehicle could have multiple cameras, microphones, etc., positioned to capture video data and audio data from that occupant.

The interior of a vehicle 410 can be a standard vehicle, an autonomous vehicle, a semi-autonomous vehicle, and so on. The vehicle can be a sedan or other automobile, a van, a sport utility vehicle (SUV), a truck, a bus, a special purpose vehicle, and the like. The interior of the vehicle 410 can include standard controls such as a steering wheel 436, a throttle control (not shown), a brake 434, and so on. The interior of the vehicle can include other controls 432 such as controls for seats, mirrors, climate controls, audio systems, etc. The controls 432 of the vehicle 410 can be controlled by a controller 430. The controller 430 can control the vehicle 410 in various manners such as autonomously, semi-autonomously, assertively to a vehicle occupant 420 or 422, etc. In embodiments, the controller provides vehicle control or manipulation techniques, assistance, etc. The controller 430 can receive instructions via an antenna 412 or using other wireless techniques. The controller 430 can be preprogrammed to cause the vehicle to follow a specific route. The specific route that the vehicle is programmed to follow can be based on the cognitive state of the vehicle occupant. The specific route can be chosen based on lowest stress, least traffic, most scenic view, shortest route, and so on.

Figure 5:
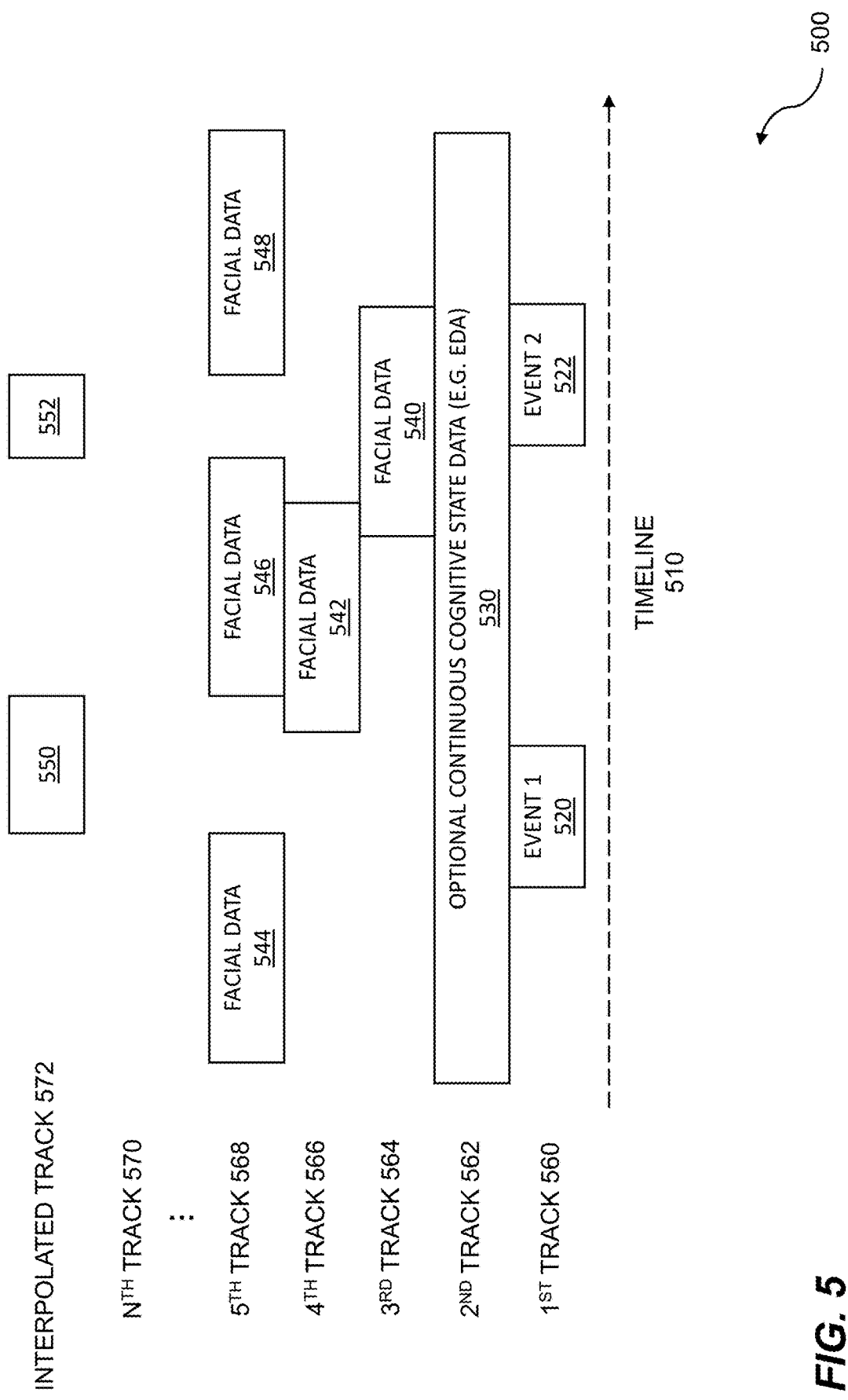
FIG. 5 is a timeline with information tracks relating to cognitive states.

FIG. 5 is a timeline with information tracks relating to cognitive states. A timeline can show one or more cognitive states that can be experienced by a vehicle occupant. The vehicle occupant can be an operator of the vehicle, a passenger of the vehicle, and so on. The timeline can be based on vehicle manipulation using cognitive state engineering. Images including facial data are obtained of a vehicle occupant. The images are analyzed to determine a cognitive state, and the cognitive state is mapped to a loading curve. The vehicle is manipulated, based on the mapping, using cognitive state alteration engineering.

The timeline 510 with information tracks 500 relates to various cognitive states. A first track 560 shows events that, in embodiments, are related to use of a computer by the individual. A first event 520 can indicate an action that the individual took (such as launching an application); an action initiated by the computer (such as the presentation of a dialog box); an external event (such as a new global positioning system (GPS) coordinate); or another event such as receiving an e-mail, a phone call, a text message, or any other type of event. In some embodiments, a photograph can be used to document an event or simply to save contextual information in the first track 560. A second event 522 can indicate another action or event in a similar manner. Such events can be used to provide contextual information and can also include information such as copies of emails, text messages, phone logs, file names, or other information that can prove useful in understanding the context of a user's actions. Thus, in embodiments, contextual information is based on one or more of a photograph, an email, a text message, a phone log, or GPS information.

A second track 562 can include continuously collected cognitive state data such as electrodermal activity data 530. A third track 564 can include facial data. The facial data can be collected intermittently when the individual is looking toward a camera. The facial data 540 can include one or more still photographs, videos, or abstracted facial expressions which can be collected when the user looks in the direction of the camera. A fourth track 566 can include facial data that is collected either intermittently or continuously by a second camera. The facial data 542 can include one or more still photographs, videos, or abstracted facial expressions which can be collected when the user looks in the direction of that camera. A fifth track 568 can include facial data that is collected from a third camera, such as the webcam. In the example shown, the fifth track 568 includes first facial data 544, second facial data 546, and third facial data 548, which can be any type of facial data including data that can be used for determining cognitive state information. Any number of samples of facial data can be collected in any track. The cognitive state data from the various tracks can be collected simultaneously, collected on one track exclusive of other tracks, collected where cognitive state data overlaps between the tracks, and so on. When cognitive state data from multiple tracks overlap, one track's data can take precedence or the data from the multiple tracks can be combined.

Additional tracks, through the $n^{th}$ track 570, of cognitive state data of any type can be collected. The additional tracks 570 can be collected on a continuous or on an intermittent basis. The intermittent basis can be either occasional or periodic. Analysis can further comprise interpolating cognitive state data when the cognitive state data collected is intermittent, and/or imputing additional cognitive state data where the cognitive state data is missing. One or more interpolated tracks 572 can be included and can be associated with cognitive state data that is collected on an intermittent basis, such as the facial data of the fifth track 568. Interpolated data 550 and further interpolated data 552 can contain interpolations of the facial data of the fifth track 568 for the time periods where no facial data was collected in that track. Other embodiments interpolate data for periods where no track includes facial data. In other embodiments, analysis includes interpolating cognitive state analysis when the cognitive state data collected is intermittent.

The cognitive state data, such as the continuous cognitive state data 530 and/or any of the collected facial data 540, 542, 544, 546, and 548, can be tagged. The tags can include metadata related to the cognitive state data, including, but not limited to, the device that collected the cognitive state data; the individual from whom the cognitive state data was collected; the task being performed by the individual; the media being viewed by the individual; and the location, environcognitive conditions, time, date, or any other contextual information. The tags can be used to locate pertinent cognitive state data; for example, the tags can be used to retrieve the cognitive state data from a database. The tags can be included with the cognitive state data that is sent over the internet to cloud or web-based storage and/or services. As such the tags can be used locally on the machine where the cognitive state data was collected and/or remotely on a remote server or a cloud/web service.

Other tags can be related to the cognitive state data. Further embodiments can include tagging the cognitive state data with sensor data. The sensor data can be obtained from the vehicle occupant along with the obtaining of the video data or the audio data, instead of the video data or the audio data, etc. In embodiments, the sensor data can include one or more of vehicle temperature, outside temperature, time of day, level of daylight, weather conditions, headlight activation, windshield wiper activation, entertainment center selection, or entertainment center volume. Other sensor data can include physiological data related to one or more occupants of the vehicle. The physiological data can include heart rate, heart rate variability, electrodermal activity, acceleration, and the like. The tags can also be related to the cognitive state that can be determined by image-based analysis of the video, audio, or physiological data, or other techniques. In embodiments, the tags that can be applied can be based on one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 6:
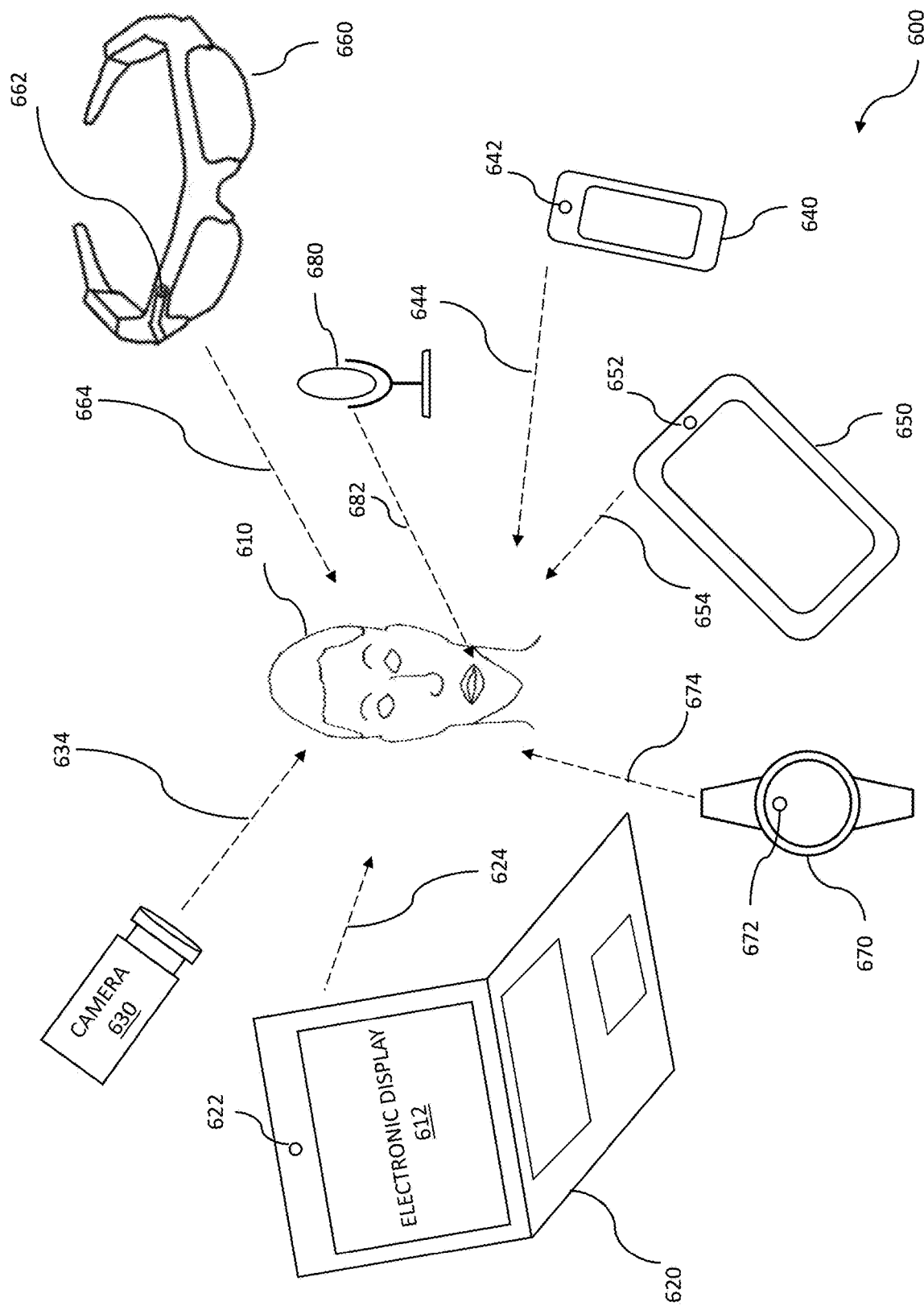
FIG. 6 shows example image and audio collection including multiple mobile devices.

FIG. 6 shows example image and audio collection including multiple mobile devices. Cognitive state data including image data, audio data, and physiological data, can be collected using multiple mobile devices. The collected cognitive state data can be used for vehicle manipulation using cognitive state engineering. Images including facial data are obtained of a vehicle occupant and analyzed to determine cognitive state. The cognitive state is mapped to a loading curve which represents a continuous spectrum of cognitive state loading. The vehicle is manipulated using cognitive state alteration engineering. While one person is shown, in practice the video data or audio data on any number of people can be collected. In the diagram 600, the multiple mobile devices can be used separately or in combination to collect video data, audio data, physiological data, or some or all of video data, audio data, and physiological data, on a user 610. While one person is shown, the video data, audio data, or physiological data can be collected on multiple people. A user 610 can be observed as she or he is performing a task, experiencing an event, viewing a media presentation, and so on. The user 610 can be shown one or more media presentations, political presentations, social media, or another form of displayed media. The one or more media presentations can be shown to a plurality of people. The media presentations can be displayed on an electronic display 612 or another display. The data collected on the user 610 or on a plurality of users can be in the form of one or more videos, video frames, and still images; one or more audio channels; etc. The plurality of video data and audio data can be of people who are experiencing different situations. Some example situations can include the user or plurality of users being exposed to TV programs, movies, video clips, social media, and other such media. The situations could also include exposure to media such as advertisements, political messages, news programs, and so on.

As previously noted, video data and audio data can be collected on one or more users in substantially identical or different situations while viewing either a single media presentation or a plurality of presentations. The data collected on the user 610 can be analyzed and viewed for a variety of purposes including expression analysis, cognitive state analysis, mental state analysis, emotional state analysis, and so on. The electronic display 612 can be on a laptop computer 620 as shown, a tablet computer 650, a cell phone 640, a television, a mobile monitor, or any other type of electronic device. In one embodiment, video data including expression data is collected on a mobile device such as a cell phone 640, a tablet computer 650, a laptop computer 620, or a watch 670. Similarly, the audio data including speech data and non-speech vocalizations can be collected on one or more of the mobile devices. Thus, the multiple sources can include at least one mobile device, such as a phone 640 or a tablet 650, or a wearable device such as a watch 670 or glasses 660. A mobile device can include a forward-facing camera and/or a rear-facing camera that can be used to collect expression data. A mobile device can include a microphone, audio transducer, or other audio capture apparatus that can be used to capture the speech and non-speech vocalizations. Sources of expression data can include a webcam 622, a phone camera 642, a tablet camera 652, a wearable camera 662, and a mobile camera 630. A wearable camera can comprise various camera devices, such as a watch camera 672. Sources of audio data 682 can include a microphone 680.

As the user 610 is monitored, the user might move due to the nature of the task, boredom, discomfort, distractions, or for another reason. As the user moves, the camera with a view of the user's face can be changed. Thus, as an example, if the user is looking in a first direction, the line of sight 624 from the webcam 622 is able to observe the user's face, but if the user is looking in a second direction, the line of sight 634 from the mobile camera 630 is able to observe the user's face. Furthermore, in other embodiments, if the user is looking in a third direction, the line of sight 644 from the phone camera 642 is able to observe the user's face, and if the user is looking in a fourth direction, the line of sight 654 from the tablet camera 652 is able to observe the user's face. If the user is looking in a fifth direction, the line of sight 664 from the wearable camera 662, which can be a device such as the glasses 660 shown which can be worn by another user or an observer, is able to observe the user's face. If the user is looking in a sixth direction, the line of sight 674 from the wearable watch-type device 670, with a camera 672 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 610 can also use a wearable device including a camera for gathering contextual information and/or collecting expression data on other users. Because the user 610 can move her or his head, the facial data can be collected intermittently when she or he is looking in a direction of a camera. In some cases, multiple people can be included in the view from one or more cameras, and some embodiments include filtering out faces of one or more other people to determine whether the user 610 is looking toward a camera. All or some of the expression data can be continuously or sporadically available from the various devices and other devices.

The captured video data can include facial expressions and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 7:
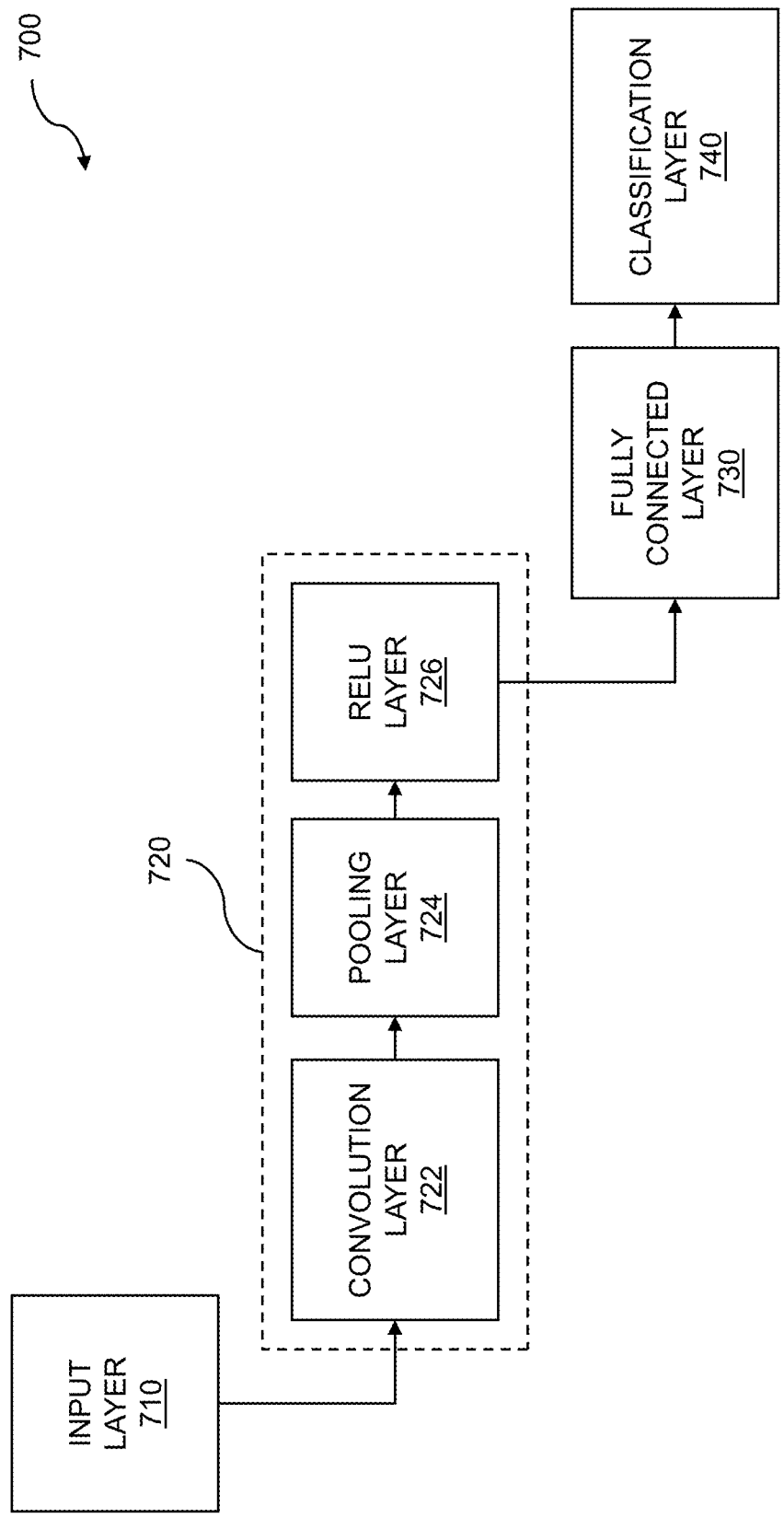
FIG. 7 is an example showing a convolutional neural network (CNN).

FIG. 7 is an example showing a convolutional neural network (CNN). A convolutional neural network such as 700 can be used for deep learning, where the deep learning can be applied to vehicle manipulation using cognitive state engineering. Images which include facial data are obtained from a vehicle occupant. Other data can be obtained including audio data and physiological data. The images are analyzed to determine a cognitive state. The cognitive state is mapped to a loading curve, and the vehicle is manipulated using cognitive state alteration engineering. The convolutional neural network can be applied to tasks such as cognitive state analysis, mental state analysis, mood analysis, emotional state analysis, and so on. Cognitive state data can include mental processes, where the mental processes can include attention, creativity, memory, perception, problem solving, thinking, use of language, or the like.

Cognitive analysis is a very complex task. Understanding and evaluating moods, emotions, mental states, or cognitive states, requires a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network which forms the basis for deep learning, is based on layers. The layers can include an input layer, a convolution layer, a fully connected layer, a classification layer, and so on. The input layer can receive input data such as image data, where the image data can include a variety of formats including pixel formats. The input layer can then perform processing tasks such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to the next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 7 is an example showing a convolutional neural network 700. The convolutional neural network can be used for deep learning, where the deep learning can be applied to cognitive state-based vehicle manipulation using near-infrared image processing. The deep learning system can be accomplished using a convolution neural network or other techniques. The deep learning can accomplish facial recognition and analysis tasks. The network includes an input layer 710. The input layer 710 receives image data. The image data can be input in a variety of formats, such as JPEG, TIFF, BMP, and GIF. Compressed image formats can be decompressed into arrays of pixels, wherein each pixel can include an RGB tuple. The input layer 710 can then perform processing such as identifying boundaries of the face, identifying landmarks of the face, extracting features of the face, and/or rotating a face within the plurality of images.

The network includes a collection of intermediate layers 720. The multilayered analysis engine can include a convolutional neural network. Thus, the intermediate layers can include a convolution layer 722. The convolution layer 722 can include multiple sublayers, including hidden layers, within it. The output of the convolution layer 722 feeds into a pooling layer 724. The pooling layer 724 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer 724. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 726. The output of the pooling layer 724 can be input to the RELU layer 726. In embodiments, the RELU layer implements an activation function such as $f(x)=\max(0,x)$, thus providing an activation with a threshold at zero. In some embodiments, the RELU layer 726 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 722 and one or more hidden layers, and wherein the multilayered analysis engine can be used for emotional analysis.

The example 700 includes a fully connected layer 730. The fully connected layer 730 processes each pixel/data point from the output of the collection of intermediate layers 720. The fully connected layer 730 takes all neurons in the previous layer and connects them to every single neuron it has. The output of the fully connected layer 730 provides input to a classification layer 740. The output of the classification layer 740 provides a facial expression and/or cognitive state as its output. Thus, a multilayered analysis engine such as the one depicted in FIG. 7 processes image data using weights, models the way the human visual cortex performs object recognition and learning, and effectively analyzes image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy, whether a voice is female, male, or robotic, whether a message is legitimate email or a "spam" message, and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt—or learn—as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and suboptimal actions are not explicitly corrected. Rather, on-line or computational performance is the focus. On-line performance includes finding a balance between exploration of new (uncharted) territory or spaces, and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include the person being more engaged, where engagement is based on affect; the person spending more time playing an online game or navigating a webpage; the person converting by buying a product or service; and so on. The reinforced learning can be based on exploring a solution space and adapting the model, algorithm, etc., which stem from outcomes of the exploration. When positive outcomes are encountered, the positive outcomes can be reinforced by changing weighting values within the model, algorithm, etc. Positive outcomes may result in increasing weighting values. Negative outcomes can also be considered, where weighting values may be reduced or otherwise adjusted.

Figure 8:
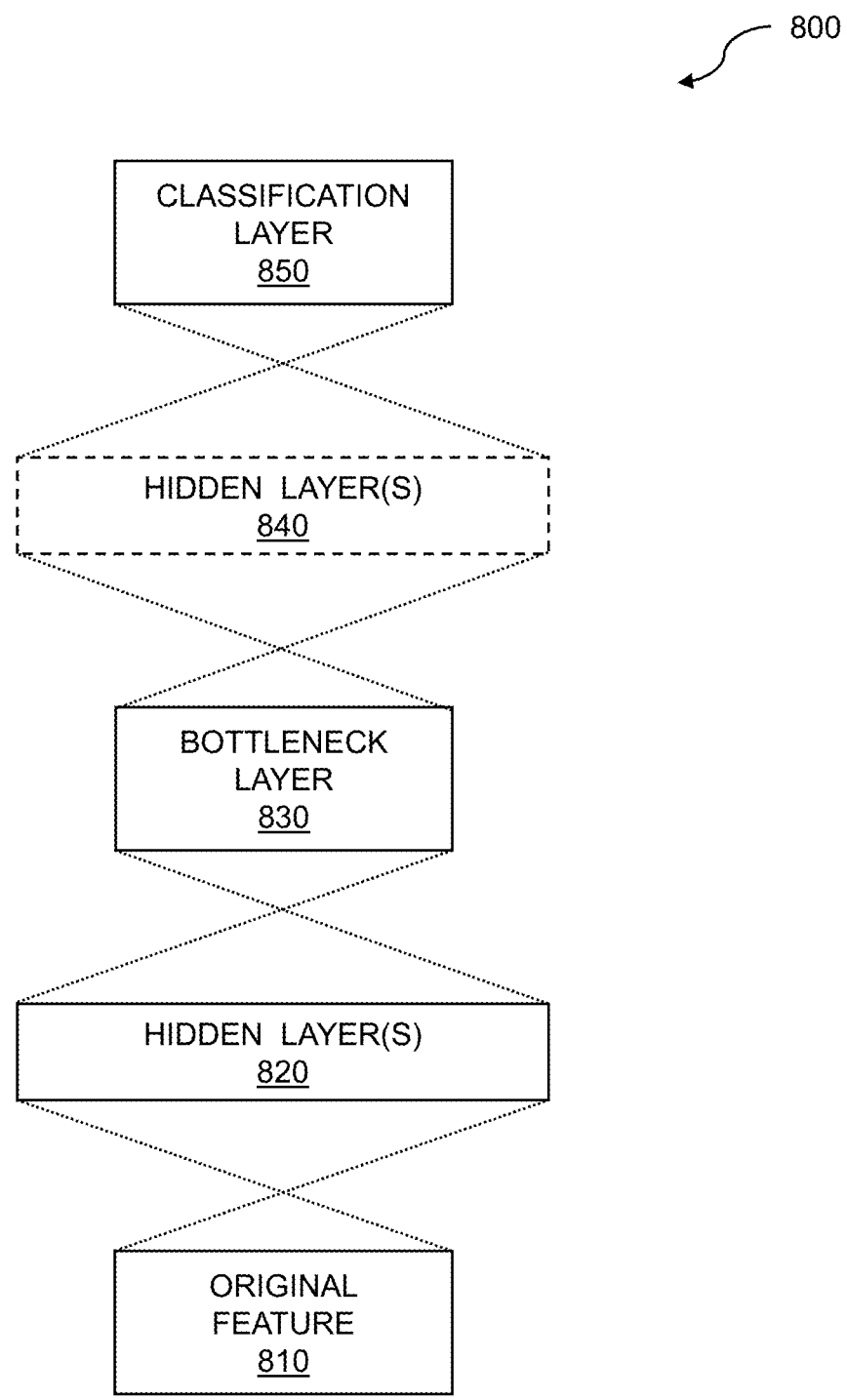
FIG. 8 illustrates a bottleneck layer within a deep learning environment.

FIG. 8 illustrates a bottleneck layer within a deep learning environment. A plurality of layers in a deep neural network (DNN) can include a bottleneck layer. The bottleneck layer can be used for vehicle manipulation using cognitive state engineering. A deep neural network can apply classifiers such as image classifiers, facial classifiers, audio classifiers, speech classifiers, physiological classifiers, and so on. The classifiers can be learned by analyzing cognitive state data. Images of a vehicle occupant are obtained, where the images include facial data. The images are analyzed to determine a cognitive state, and the cognitive state is mapped to a loading curve. The loading curve represents a continuous spectrum of cognitive state loading variation. The vehicle is manipulated based on the mapping. The manipulating is accomplished using cognitive state alteration engineering.

Layers of a deep neural network can include a bottleneck layer 800. A bottleneck layer can be used for a variety of applications such as facial recognition, voice recognition, emotional state recognition, and so on. The deep neural network in which the bottleneck layer is located can include a plurality of layers. The plurality of layers can include an original feature layer 810. A feature such as an image feature can include points, edges, objects, boundaries between and among regions, properties, and so on. The deep neural network can include one or more hidden layers 820. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to a different emotional face or voice. In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 830. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised technique. The supervised technique can include training the deep neural network with a known dataset. The features can be extracted from an autoencoder such as a variational autoencoder, a generative autoencoder, and so on. The deep neural network can include hidden layers 840. The number of the hidden layers can include zero hidden layers, one hidden layer, a plurality of hidden layers, and so on. The hidden layers following the bottleneck layer can include more nodes than the bottleneck layer. The deep neural network can include a classification layer 850. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 9:
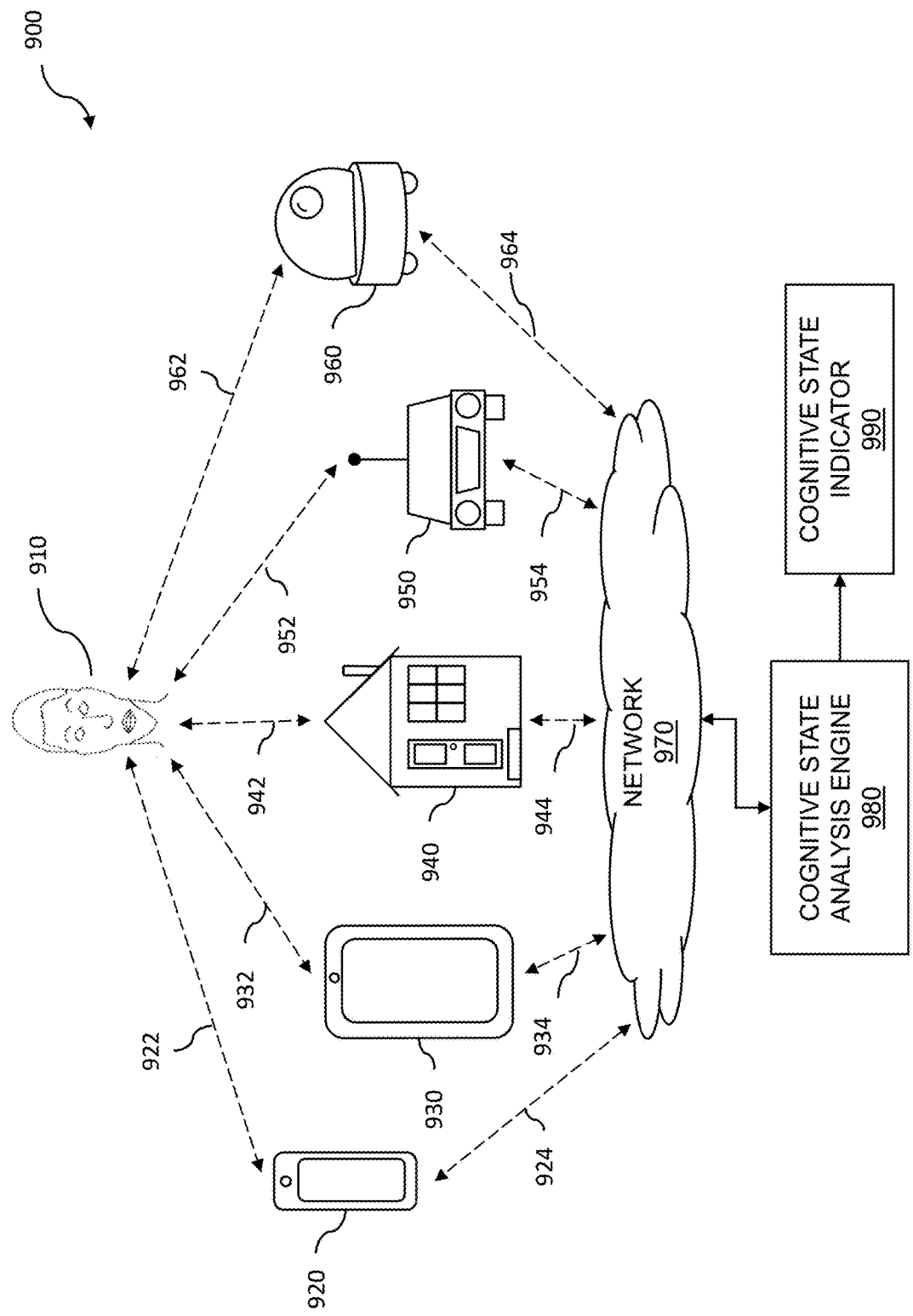
FIG. 9 shows data collection including devices and locations.

FIG. 9 shows data collection including devices and locations 900. Data, including video data, audio data, and physio data, can be obtained for vehicle manipulation using cognitive state engineering. The data can be obtained from multiple devices, vehicles, and locations. Images including facial data of a vehicle occupant are obtained using imaging devices. The images can include visible light-based images and near-infrared based images. A computing device is used to analyze the images to determine cognitive state. The cognitive state is mapped to a loading curve that represents a continuous spectrum of cognitive state loading. The vehicle is manipulated using cognitive state alteration engineering.

The multiple mobile devices, vehicles, and locations 900 can be used separately or in combination to collect video data on a user 910. The video data can include facial data. Other data such as audio data, physiological data, and so on, can be collected on the user. While one person is shown, the video data, or other data, can be collected on multiple people. A user 910 can be observed as she or he is performing a task, experiencing an event, viewing a media presentation, and so on. The user 910 can be shown one or more media presentations, political presentations, social media, or another form of displayed media. The one or more media presentations can be shown to a plurality of people. The media presentations can be displayed on an electronic display coupled to a client device. The data collected on the user 910 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As previously noted, video data can be collected on one or more users in substantially identical or different situations and viewing either a single media presentation or a plurality of presentations. The data collected on the user 910 can be analyzed and viewed for a variety of purposes including expression analysis, mental state analysis, cognitive state analysis, and so on. The electronic display can be on a smartphone 920 as shown, a tablet computer 930, a personal digital assistant, a television, a mobile monitor, or any other type of electronic device. In one embodiment, expression data is collected on a mobile device such as a cell phone 920, a tablet computer 930, a laptop computer, or a watch. Thus, the multiple sources can include at least one mobile device, such as a phone 920 or a tablet 930, or a wearable device such as a watch or glasses (not shown). A mobile device can include a front-facing camera and/or a rear-facing camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 910, data can be collected in a house 940 using a web camera or the like; in a vehicle 950 using a web camera, client device, etc.; by a social robot 960, and so on.

As the user 910 is monitored, the user 910 might move due to the nature of the task, boredom, discomfort, distractions, or for another reason. As the user moves, the camera with a view of the user's face can be changed. Thus, as an example, if the user 910 is looking in a first direction, the line of sight 922 from the smartphone 920 is able to observe the user's face, but if the user is looking in a second direction, the line of sight 932 from the tablet 930 is able to observe the user's face. Furthermore, in other embodiments, if the user is looking in a third direction, the line of sight 942 from a camera in the house 940 is able to observe the user's face, and if the user is looking in a fourth direction, the line of sight 952 from the camera in the vehicle 950 is able to observe the user's face. If the user is looking in a fifth direction, the line of sight 962 from the social robot 960 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 910 can also use a wearable device including a camera for gathering contextual information and/or collecting expression data on other users. Because the user 910 can move her or his head, the facial data can be collected intermittently when she or he is looking in a direction of a camera. In some cases, multiple people can be included in the view from one or more cameras, and some embodiments include filtering out faces of one or more other people to determine whether the user 910 is looking toward a camera. All or some of the expression data can be continuously or sporadically available from the various devices and other devices.

The captured video data can include cognitive content, such as facial expressions, etc., and can be transferred over a network 970. The network can include the Internet or other computer network. The smartphone 920 can share video using a link 924, the tablet 930 using a link 934, the house 940 using a link 944, the vehicle 950 using a link 954, and the social robot 960 using a link 964. The links 924, 934, 944, 954, and 964 can be wired, wireless, and hybrid links. The captured video data, including facial expressions, can be analyzed on a cognitive state analysis engine 980, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capture device. The analysis data from the cognitive state analysis engine can be processed by a cognitive state indicator 990. The cognitive state indicator 990 can indicate cognitive states, mental states, moods, emotions, etc. In embodiments, the cognitive state can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 10A:
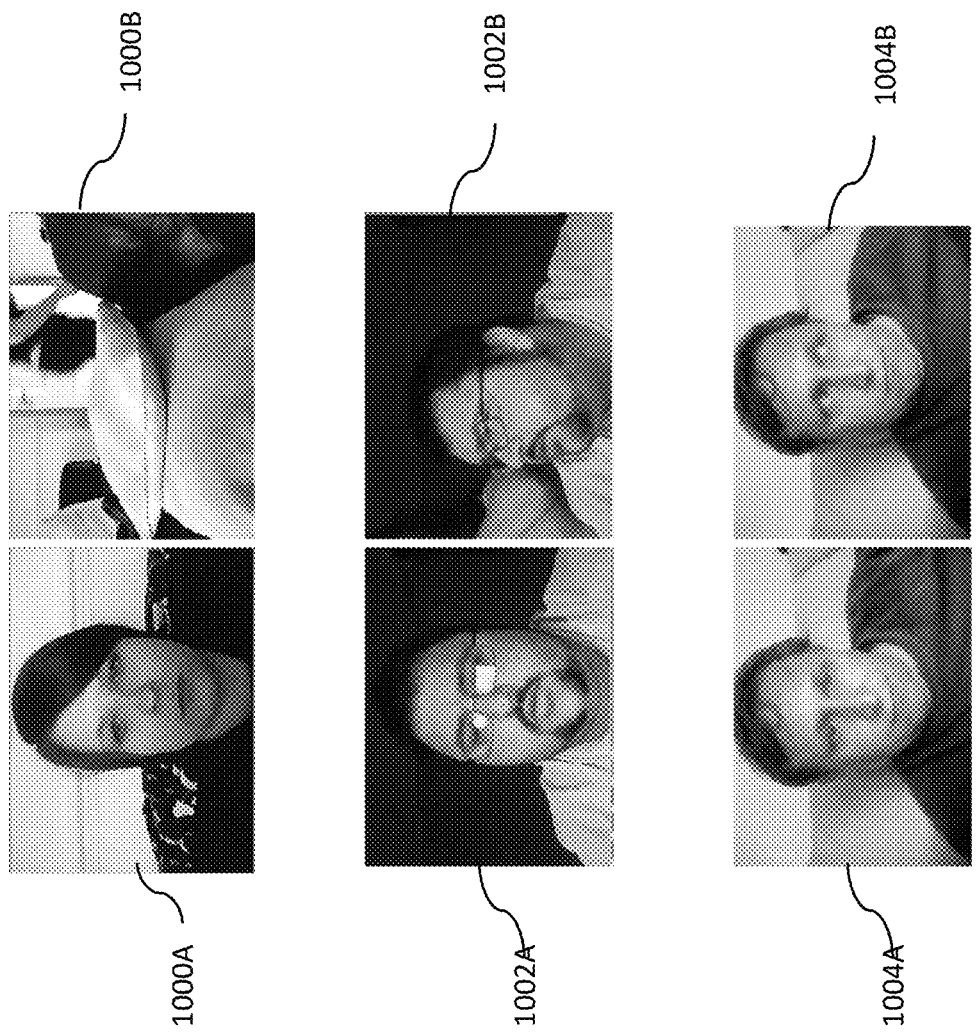
FIG. 10A is an example showing display attendance.

FIG. 10A shows examples of display attendance. In FIG. 10A, there are three sets of images. Each set of images is from an individual undergoing an attendance query evaluation session. Image 1000A shows a first individual at a first time during presentation of video content. In image 1000A, the first individual is watching the content. Image 1000B shows a view of the first individual at a second time during presentation of video content. Image 1000B indicates that the individual has left the area, and thus, is no longer viewing the content. Using face detection, it is possible to accurately detect when the viewer's departure occurs.

Image 1002A shows a second individual at a first time during presentation of video content. In image 1002A, the second individual is watching the content. Image 1002B shows a view of the second individual at a second time during presentation of video content. Image 1002B indicates that the second individual has turned his head and is no longer facing the content, and thus, the second individual is no longer viewing the content. Embodiments use head pose estimation, which determines the position of the head in 3D space, making it possible to infer if the person is facing the screen and at what angle they are facing the screen. This is not a binary measure, but rather an analog measure depending on head angle.

Image 1004A shows a third individual at a first time during presentation of video content. In image 1004A, the third individual is watching the content. Image 1004B shows a view of the third individual at a second time during presentation of video content. Image 1004B indicates that the third individual, while still facing the screen, has averted his eyes, and thus his eyes are no longer directed towards the content, and accordingly, the third individual is no longer viewing the content. Thus, even if the person is present and facing the screen, it is possible that the person's gaze is averted away from the content. This can occur when a person is texting on the phone while the content is playing. To determine if the eyes are focused on the screen showing the content of interest, embodiments utilize a method that learns the location of the pupils within the eye, and combines this with both head pose information and an assumption about the location of the camera with respect to the screen, to infer whether the eyes are looking at or away from the screen. Note that the aforementioned eye gaze processing is different from (and much less computation-intensive than) eye tracking, which can require special hardware and an extensive calibration step as well as controlled settings in regard to lighting and other factors. Even in the case of webcam-based eye tracking, a calibration step and strict standards for lighting are required. Also, if the person moves their face or body, re-calibration is required. While this eye tracking works in controlled "lab" environments, it has not proved feasible for spontaneous, natural viewing environments where a consumer is naturally watching a video. Thus, in embodiments, analyzing the plurality of images is accomplished without eye tracking. Rather, eye gaze or gaze tracking, can be used for cognitive load estimation. Eye gaze is one of the most salient modalities for estimating cognitive load. Some embodiments comprise estimating a cognitive load based on eye gaze tracking.

Figure 10B:
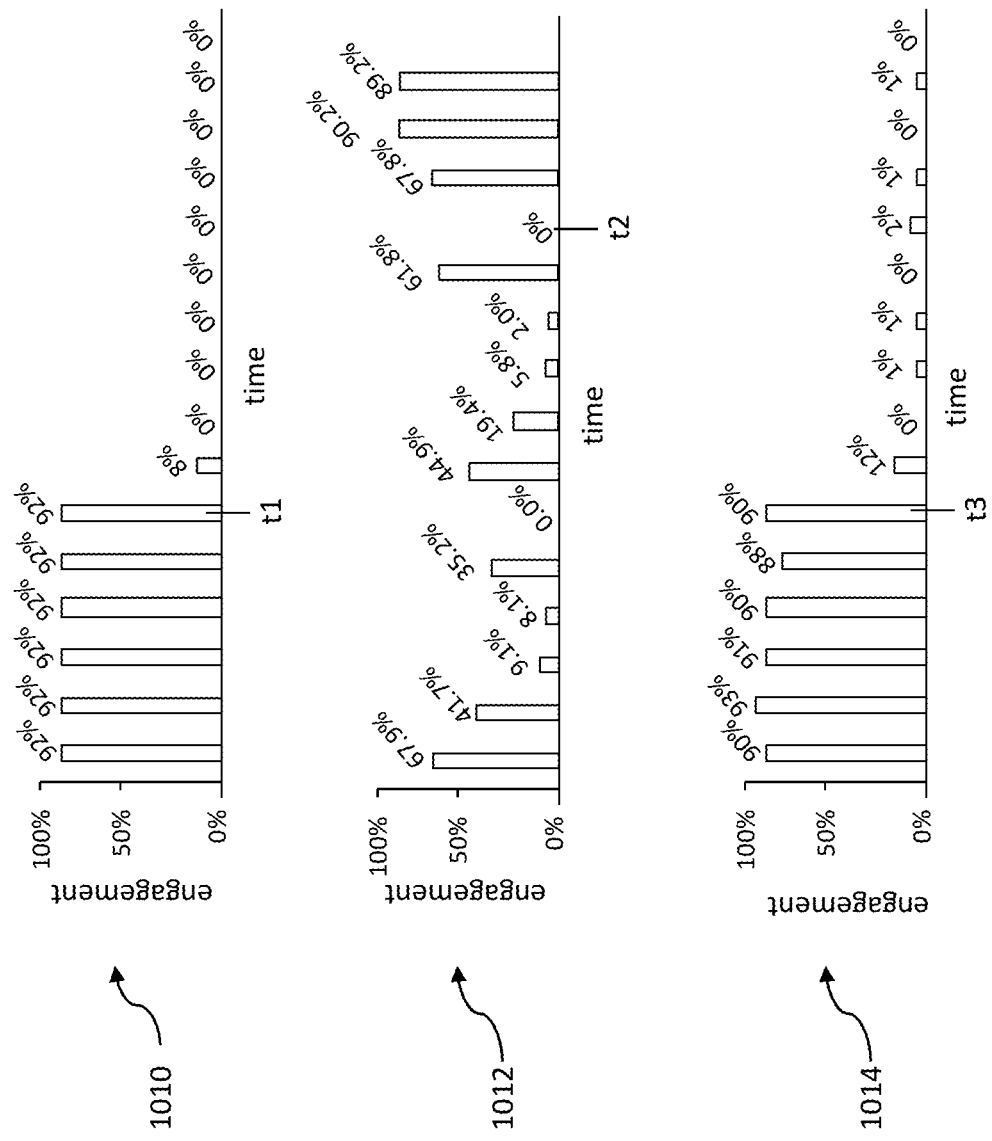
FIG. 10B is an example illustrating facial data.

FIG. 10B is an example illustrating facial data. FIG. 10B includes three charts, charts 1010, 1012, and 1014. Each chart has a horizontal axis of time, and a vertical axis of an engagement level. Each bar on the chart may represent a time window comprising a fixed unit of time, such as one minute. The chart 1010 corresponds to the sequence of images 1000A and 1000B of FIG. 10A. Up until time t1, the engagement level is at 92%, indicating that the user is mostly focused on the displayed content. After time t1, the next bar indicates a very low engagement level because at some point during that time window, the user left the area. In the subsequent time windows, the engagement level is zero, as the individual is no longer present.

The chart 1012 corresponds to the sequence of images 1002A and 1002B of FIG. 10A. In this example, the individual remains present in front of the rendered content, but for a portion of the video, he frequently looks away. As can be seen in the chart 1012, up until time t2, the engagement level is sporadic, fluctuating between low and midrange levels. After time t2, the engagement level increases. In such an embodiment where digital media content is modified based on viewership, a chart such as 1012 indicates that the ending of the video is engaging to the individual, while earlier in the video, before time t2, the video was not as engaging. Thus, in embodiments, the modification includes shortening the video by deleting and/or shortening scenes of the video prior to time t2, in order to better hold the individual's attention and interest.

The chart 1014 corresponds to the sequence of images 1004A and 1004B of FIG. 10A. In this example, the individual remains present in front of the rendered content, but for a portion of the video, he is frequently looking away by averting his gaze away from the screen that is presenting the media content. As can be seen in chart 1014, up until time t3, the engagement level is relatively high, indicating a high level of focus by the individual on the media content. After time t3, the engagement level significantly decreases. In such an embodiment where digital media content is modified based on viewership, a chart such as 1014 indicates that the beginning of the video is engaging to the individual, while later in the video, after time t3, the video was not as engaging. Thus, in embodiments, the modification includes shortening the video by deleting and/or shortening scenes after time t3, in order to better hold the individual's attention and interest. In this way, the information obtained by disclosed embodiments can help tailor media content to be more engaging and effective.

Figure 11:
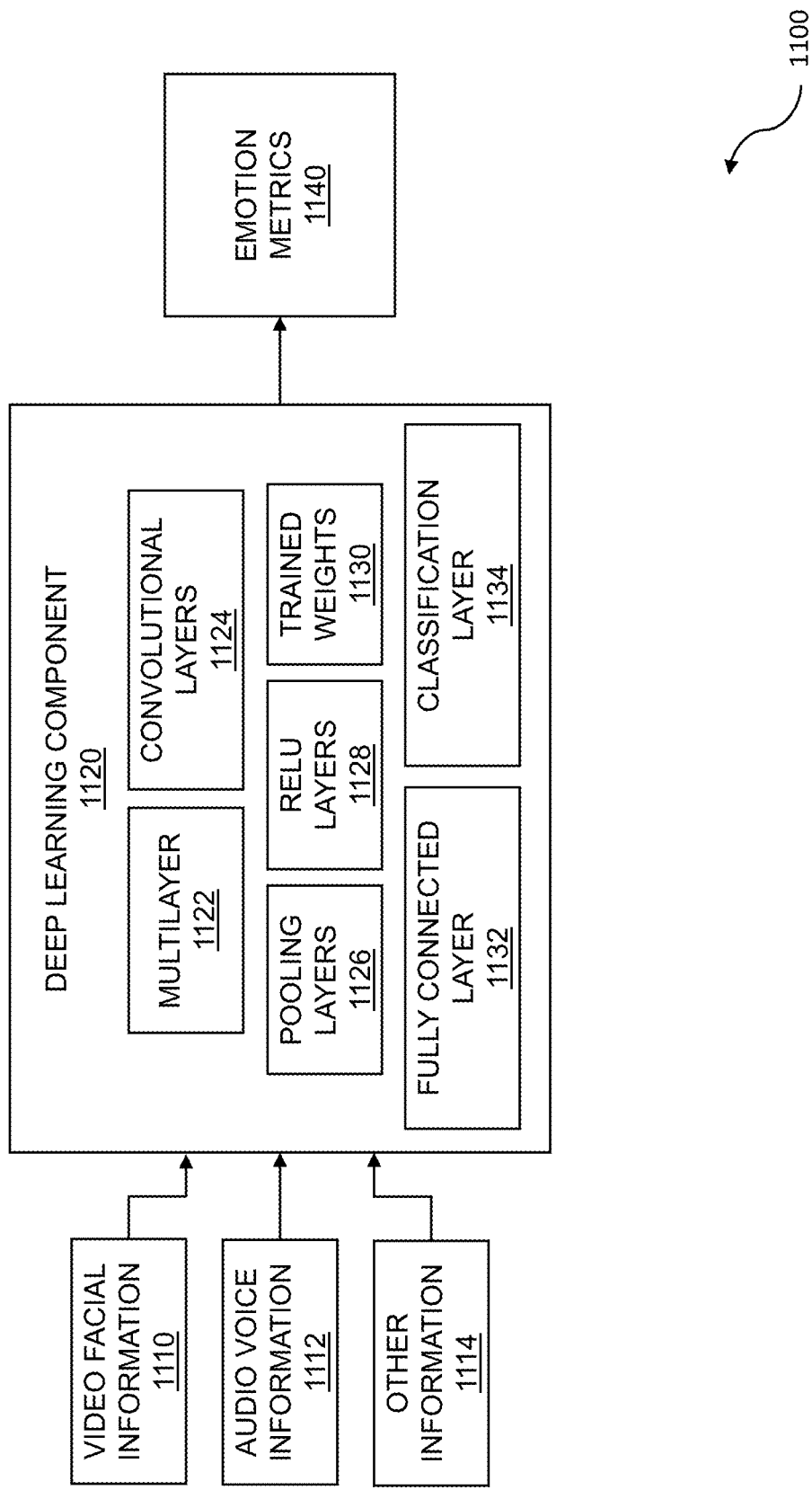
FIG. 11 illustrates a high-level diagram for deep learning.

FIG. 11 illustrates a high-level diagram for deep learning. Deep learning can be used for facial tracking with classifiers for query evaluation. A plurality of information channels is captured into a computing device such as a smartphone, personal digital assistant (PDA), tablet, laptop computer, and so on. The plurality of information channels includes contemporaneous audio information and video information from an individual. Trained weights are learned on a multilayered convolutional computing system. The trained weights are learned using the audio information and the video information from the plurality of information channels. The trained weights cover both the audio information and the video information and are trained simultaneously. The learning facilitates emotion analysis of the audio information and the video information. Further information is captured into a second computing device. The second computing device and the first computing device may be the same computing device. The further information can include physiological information, contextual information, and so on. The further information is analyzed using the trained weights to provide an emotion metric based on the further information.

Understanding and evaluating moods, emotions, or mental states requires a nuanced evaluation of facial expressions, audio expressions, or other cues generated by people. Mental state analysis is important in many areas such as research, psychology, business, intelligence, law enforcement, and so on. The understanding of mental states can be used in a variety of fields, such as improving marketing analysis, assessing the effectiveness of customer service experiences and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues.

Deep learning is a branch of machine learning which seeks to imitate in software the activity which takes place in layers of neurons in the neocortex of the human brain. Deep learning applications include processing of image data, audio data, and so on. FIG. 11 illustrates a high-level diagram for deep learning 1100. The deep learning can be accomplished using a multilayered convolutional computing system, a convolutional neural network, or other techniques. The deep learning can accomplish image analysis, audio analysis, and other analysis tasks. A deep learning component 1120 collects and analyzes various types of information from a plurality of information channels. The information channels can include video facial information 1110, audio voice information 1112, other information 1114, and so on. In embodiments, the other information can include one or more of electrodermal activity, heart rate, heart rate variability, skin temperature, blood pressure, muscle movements, or respiration.

Returning to the deep learning component 1120, the deep learning component can include a multilayered convolutional computing system 1122. The multilayered convolutional computing system 1122 can include a plurality of layers of varying types. The layers can include one or more convolutional layers 1124 which can be used for learning and analysis. The convolutional layers can include pooling layers 1126 which can combine the outputs of clusters into a single datum. The layers can include one or more Rectified Linear Unit (ReLU) layers 1128. The one or more ReLU layers can implement an activation function such as $f(x)= max(0,x)$, thus providing an activation with a threshold at zero. The convolutional layers can include trained weights 1130. The trained weights can be based on learning, where the learning uses information collected from one or more individuals via a plurality of information channels. The trained weights can be used to enable the multilayer convolutional computing system to determine image characteristics, voice characteristics, and so on.

The deep learning component 1120 can include a fully connected layer 1132. The fully connected layer 1132 processes each data point from the output of a collection of intermediate layers. The fully connected layer 1132 takes all data points in the previous layer and connects them to every single node contained within the fully connected layer. The output of the fully connected layer 1132 can provide input to a classification layer 1134. The classification layer can be used to classify emotional states, mental states, moods, and so on. The classification can be based on using classifiers. The deep learning component 1120 provides data that includes emotion metrics 1140. The emotion metrics can include an emotion type, a number of occurrences of the emotional type, the intensity of the emotional type, and so on. The emotion metric can be based on a threshold value, on a target value, on a goal, etc. The emotion metric can be based on emotion types that can occur over a period of time. More than one emotion metric can be provided.

Figure 12:
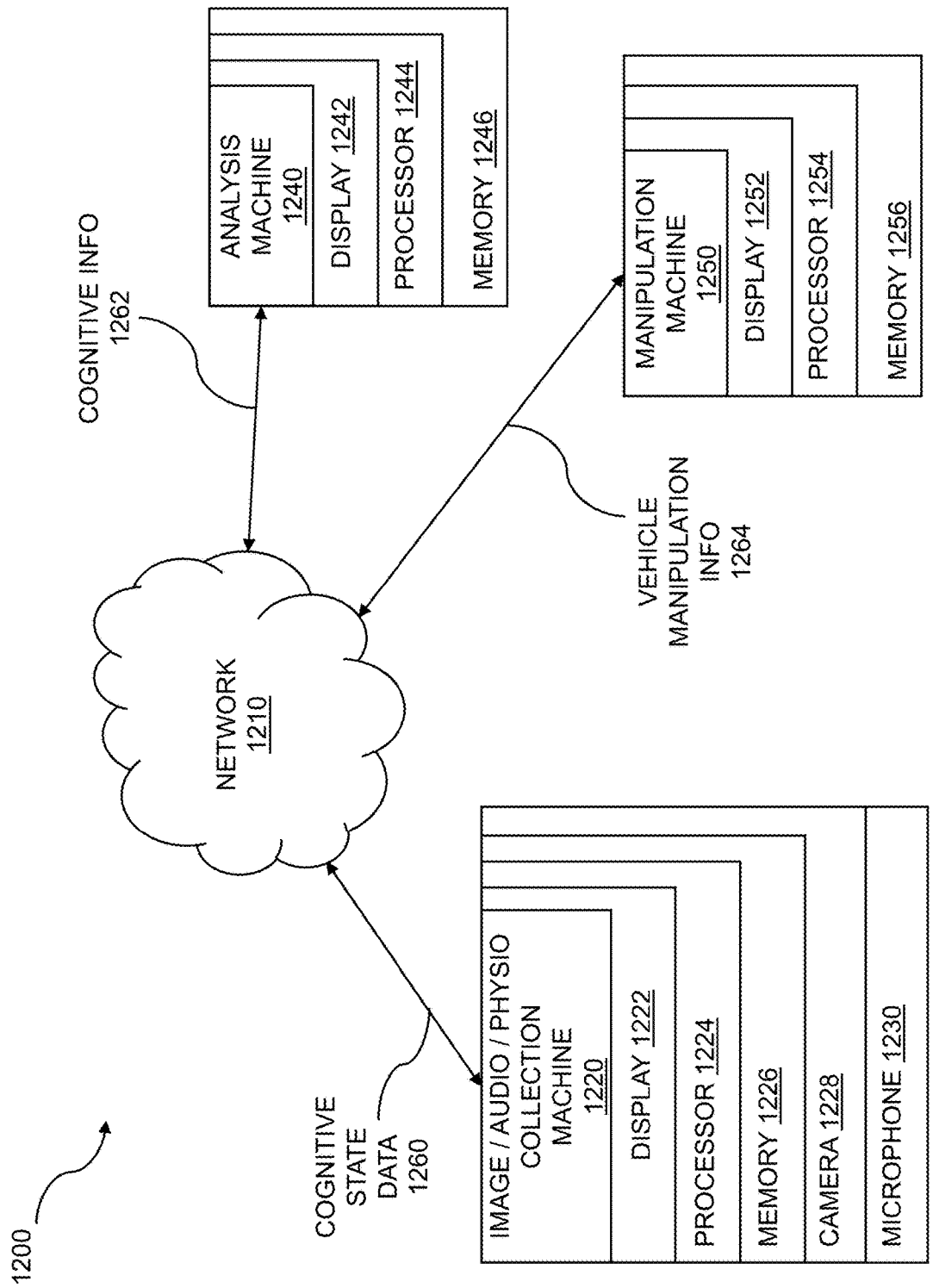
FIG. 12 is a diagram of a system for vehicle manipulation using cognitive state engineering.

FIG. 12 is a diagram of a system 1200 for vehicle manipulation using cognitive state engineering. Cognitive state engineering can use analysis of images, audio data, or physiological data. Images of a vehicle occupant are obtained using one or more imaging devices within a vehicle. The one or more images include facial data of the vehicle occupant. A computing device is used to analyze the images to determine a cognitive state. The cognitive state is mapped to a loading curve, where the loading curve represents a continuous spectrum of cognitive state loading variation. The vehicle is manipulated based on the mapping to the loading curve, where the manipulating is accomplished using cognitive state alteration engineering. Audio information can be obtained from the occupant of the vehicle and can augment the analyzing based on the audio information. Physiological information can be obtained from the occupant of the vehicle and can augment the analyzing based on the physiological information.

The network 1210, Internet, intranet, or another computer network, can be used for communication among various machines. An image, audio, and physio collection machine 1220 has a memory 1226 which stores instructions and one or more processors 1224 coupled to the memory 1226, wherein the one or more processors 1224 can execute instructions. The image, audio, and physio collection machine 1220 can also have a network connection to carry cognitive state data 1260, and a display 1222 that can present cognitive state data, cognitive state profiles, mental state data, mental state profiles, emotional states, emotional state profiles, and so on. The image, audio, and physio collection machine 1220 can collect cognitive state data including image data, facial data, voice data, audio data, physiological data, etc., from an occupant of a vehicle. In some embodiments, there are multiple image, audio, and physio collection machines 1220 that each collect cognitive state data including facial data. This type of collection machine can have a camera 1228, a microphone 1230, or other sensors. In many embodiments, a camera, a microphone, and physiological sensors will be present. Other embodiments include obtaining audio information and augmenting the analyzing of the cognitive state data with the audio information. The audio data can include speech or non-speech vocalizations. Further embodiments include obtaining physiological information from the occupant of the vehicle and augmenting the analyzing based on the physiological information. The physiological data can include as heart rate, heart rate variability, respiration rate, skin conductivity, and so on. Once the cognitive state data 1260 has been collected, the image, audio, and physio collection machine 1220 can upload information to an analysis machine 1240, based on the cognitive state data from the occupant of the vehicle. The image, audio, and physio collection machine 1220 can communicate with the analysis machine 1240 over the network 1210, the Internet, some other computer network, or by another method suitable for communication between two machines. In some embodiments, the analysis machine 1240 functionality is embodied in the image and audio collection machine 1220.

The analysis machine 1240 can have a network connection for cognitive states or cognitive state information 1262, a display 1242, a memory 1246 which stores instructions, and one or more processors 1244 coupled to the memory 1246, wherein the one or more processors 1244 can execute instructions. The analysis machine 1240 can receive cognitive state information, collected from an occupant of the vehicle, from the image, audio, and physio collection machine 1220, and can learn a cognitive state profile for the occupant. The analysis machine 1240 can also compare further cognitive state data with the cognitive state profile while the occupant is in a second vehicle. In some embodiments, the analysis machine 1240 also allows a user to view and evaluate the cognitive state data and cognitive state profiles for the occupant of the vehicle. The analysis machine 1240 can then provide the cognitive state information 1262, including cognitive state profile information, to the manipulation machine 1250. In some embodiments, the image, audio, and physio collection machine 1220 can also function as the manipulation machine 1250. In further embodiments, the cognitive state data that was analyzed can be based on intermittent obtaining of images that include facial data.

The manipulation machine 1250 can have a memory 1256 which stores instructions, and one or more processors 1254 attached to the memory 1256, wherein the one or more processors 1254 can execute instructions. The manipulation machine can use a computer network, the Internet, or another computer communication method, to request the cognitive state information 1262 from the analysis machine. The manipulation machine 1250 can receive vehicle manipulation information 1264, based on the cognitive state data 1260, from the occupant of the vehicle. The cognitive state information and vehicle manipulation information for the occupant can be presented on a display 1252. In some embodiments, the manipulation machine is set up to receive cognitive state data collected from an occupant of the vehicle, in a real-time or near real-time embodiment. In other embodiments, the manipulation machine is set up to receive the cognitive state data on an intermittent basis. In at least one embodiment, a single computer incorporates the image and audio collection machine, the analysis machine, and the navigation machine functionalities.

In embodiments, a computer program product embodied in a non-transitory computer readable medium for vehicle manipulation, the computer program product comprising code which causes one or more processors to perform operations of: obtaining one or more images of a vehicle occupant using one or more imaging devices within a vehicle, wherein the one or more images include facial data of the vehicle occupant; analyzing, using a computing device, the one or more images to determine a cognitive state; mapping the cognitive state to a loading curve, wherein the loading curve represents a continuous spectrum of cognitive state loading variation; and manipulating the vehicle, based on the mapping to the loading curve, wherein the manipulating is accomplished using cognitive state alteration engineering.

Each of the above methods may be executed on one or more processors on one or more computer systems. Embodiments may include various forms of distributed computing, client/server computing, and cloud-based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random-access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples but is to be understood in the broadest sense allowable by law.

What is claimed is:

1. A computer-implemented method for vehicle manipulation comprising:
   obtaining one or more images of a vehicle occupant using one or more imaging devices within a vehicle, wherein the one or more images include facial data of the vehicle occupant;
   analyzing, using a computing device, the one or more images to determine a cognitive state;
   mapping the cognitive state to a loading curve, wherein the loading curve represents a continuous spectrum of cognitive state loading variation, wherein the spectrum of cognitive state loading variation comprises a range from very underloaded to very overloaded; and
   manipulating the vehicle, based on the mapping to the loading curve, wherein the manipulating is accomplished using cognitive state alteration engineering.

2. The method of claim 1 further comprising obtaining additional images of one or more additional occupants of the vehicle, wherein the additional images are analyzed to determine one or more additional cognitive states.

3. The method of claim 2 further comprising adjusting the mapping of the cognitive state, wherein the adjusting is performed using the additional cognitive states.

4. The method of claim 3 further comprising changing the manipulating the vehicle based on the adjusting.

5. The method of claim 1 wherein the analyzing is performed beyond eye region input from the one or more images.

6. The method of claim 1 wherein the spectrum of cognitive state loading variation comprises a bell curve function.

7. The method of claim 6 wherein the bell curve function represents a Yerkes-Dodson law curve.

8. The method of claim 1 wherein the manipulating includes changing vehicle occupant sensory stimulation.

9. The method of claim 8 wherein the sensory stimulation includes aural, visual, or haptic stimulation.

10. The method of claim 1 wherein the vehicle occupant is a driver of the vehicle.

11. The method of claim 1 further comprising obtaining audio information from the occupant of the vehicle and augmenting the analyzing based on the audio information.

12. The method of claim 11 wherein the audio information includes speech.

13. The method of claim 11 wherein the audio information includes non-speech vocalizations.

14. The method of claim 13 wherein the non-speech vocalizations include grunts, yelps, squeals, snoring, sighs, laughter, filled pauses, unfilled pauses, or yawns.

15. The method of claim 1 further comprising obtaining physiological information from the occupant of the vehicle and augmenting the analyzing based on the physiological information.

16. The method of claim 1 wherein the analyzing is performed using deep learning.

17. The method of claim 16 wherein the learning is performed using a deep neural network.

18. The method of claim 16 wherein the learning is performed using a convolutional neural network.

19. The method of claim 16 wherein the learning is performed using a recurrent neural network.

20. The method of claim 1 further comprising tagging cognitive state data with sensor data from the vehicle.

21. The method of claim 20 wherein the sensor data includes one or more of vehicle temperature, outside temperature, time of day, level of daylight, weather conditions, headlight activation, windshield wiper activation, entertainment center selection, entertainment center volume, etc.

22. The method of claim 1 wherein the cognitive state includes drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

23. The method of claim 1 wherein the cognitive state that was analyzed is based on intermittent obtaining of images that include facial data.

24. The method of claim 1 further comprising estimating a cognitive load based on eye gaze tracking.

25. A computer program product embodied in a non-transitory computer readable medium for vehicle manipulation, the computer program product comprising code which causes one or more processors to perform operations of:
   obtaining one or more images of a vehicle occupant using one or more imaging devices within a vehicle, wherein the one or more images include facial data of the vehicle occupant;
   analyzing, using a computing device, the one or more images to determine a cognitive state;
   mapping the cognitive state to a loading curve, wherein the loading curve represents a continuous spectrum of cognitive state loading variation, wherein the spectrum of cognitive state loading variation comprises a range from very underloaded to very overloaded; and
   manipulating the vehicle, based on the mapping to the loading curve, wherein the manipulating is accomplished using cognitive state alteration engineering.

26. A computer system for vehicle manipulation comprising:
- a memory which stores instructions;
- one or more processors coupled to the memory wherein the one or more processors, when executing the instructions which are stored, are configured to:
  - obtain one or more images of a vehicle occupant using one or more imaging devices within a vehicle, wherein the one or more images include facial data of the vehicle occupant;
  - analyze, using a computing device, the one or more images to determine a cognitive state;
  - map the cognitive state to a loading curve, wherein the loading curve represents a continuous spectrum of cognitive state loading variation, wherein the spectrum of cognitive state loading variation comprises a range from very underloaded to very overloaded; and
  - manipulate the vehicle, based on mapping to the loading curve, wherein the manipulating is accomplished using cognitive state alteration engineering.

* * * * *